US012802823B2

(12) United States Patent
Nakano et al.

(10) Patent No.: US 12,802,823 B2
(45) Date of Patent: Nov. 17, 2026

(54) IMAGE PROCESSING APPARATUS, IMAGE PROCESSING METHOD, AND NON-TRANSITORY COMPUTER-READABLE STORAGE MEDIUM

(71) Applicant: NEC Corporation, Tokyo (JP)

(72) Inventors: Gaku Nakano, Tokyo (JP); Shoji Nishimura, Tokyo (JP); Yoshitaka Higeta, Tokyo (JP); Youtarou Noda, Tokyo (JP); Shigeki Shinoda, Tokyo (JP); Yuzo Senda, Tokyo (JP); Shin Tominaga, Tokyo (JP); Masumi Ishikawa, Tokyo (JP); Daisuke Ikefuji, Tokyo (JP); Kana Takizawa, Tokyo (JP); Kenichi Ishii, Tokyo (JP); Yoshiyuki Satou, Tokyo (JP); Eishi Arita, Tokyo (JP); Shota Yamamoto, Tokyo (JP); Shinya Yamasaki, Tokyo (JP); Narumitsu Notomi, Tokyo (JP); Aki Nakamura, Tokyo (JP)

(73) Assignee: NEC CORPORATION, Tokyo (JP)

( * ) Notice: Subject to any disclaimer, the term of this patent is extended or adjusted under 35 U.S.C. 154(b) by 70 days.

(21) Appl. No.: 18/954,905

(22) Filed: Nov. 21, 2024

(65) Prior Publication Data

US 2025/0087368 A1 Mar. 13, 2025

Related U.S. Application Data

(63) Continuation of application No. 18/007,969, filed as application No. PCT/JP2021/015553 on Apr. 15, 2021, now Pat. No. 12,176,112.

(30) Foreign Application Priority Data

Jun. 5, 2020 (JP) ................................ 2020-098402

(51) Int. Cl.

*G16H 50/30* (2018.01)
*G06T 7/60* (2017.01)
*G07C 9/10* (2020.01)

(52) U.S. Cl.

CPC ............... *G16H 50/30* (2018.01); *G06T 7/60* (2013.01); *G07C 9/10* (2020.01); *G06T 2207/30196* (2013.01); *G06T 2207/30242* (2013.01)

(58) Field of Classification Search

None
See application file for complete search history.

(56) References Cited

U.S. PATENT DOCUMENTS 10,572,738 B2 * 2/2020 Leizerovich ........... G06V 20/40
11,747,443 B2 * 9/2023 Ramesh .................. G01S 13/56
342/126

(Continued)

FOREIGN PATENT DOCUMENTS

AU 2012257871 A1 * 11/2013 ............... G07C 9/10
CN 101321272 A * 12/2008

(Continued)

OTHER PUBLICATIONS

International Search Report for PCT Application No. PCT/JP2021/015553, mailed on Jul. 6, 2021.

(Continued)

*Primary Examiner* — Fekadeselassie Girma
(74) *Attorney, Agent, or Firm* — Sughrue Mion, PLLC

(57) ABSTRACT

An image processing apparatus includes at least one memory configured to store instructions, and at least one processor configured to execute the instructions to process an image of a target region, and thereby compute a proximity index being an index relating to a proximity state of a plurality of persons captured in the image, and cause a (Continued)

predetermined apparatus to execute predetermined control, when the proximity index satisfies a criterion.

8 Claims, 24 Drawing Sheets

(56) References Cited

U.S. PATENT DOCUMENTS

| | | | | |
|---|---|---|---|---|
| 2012/0020518 | A1* | 1/2012 | Taguchi | G06T 7/292<br>382/103 |
| 2016/0188962 | A1* | 6/2016 | Taguchi | G06V 40/193<br>382/117 |
| 2017/0004629 | A1* | 1/2017 | Zhao | G06T 7/20 |
| 2020/0058167 | A1* | 2/2020 | Morisawa | G06T 15/20 |
| 2020/0151881 | A1* | 5/2020 | Dodd | G06T 7/11 |
| 2020/0242575 | A1* | 7/2020 | Shell | G06Q 10/02 |
| 2026/0075335 | A1* | 3/2026 | Jin | H04N 25/63 |

FOREIGN PATENT DOCUMENTS

| | | | | | |
|---|---|---|---|---|---|
| CN | 207228938 | U | | 4/2018 | |
| CN | 109584409 | A | | 4/2019 | E01F 13/06 |
| CN | 109712719 | A | | 5/2019 | |
| CN | 110047173 | A | | 7/2019 | |
| CN | 110069973 | A | | 7/2019 | B25J 9/0003 |
| CN | 209208670 | U | * | 8/2019 | |
| CN | 111005647 | A | | 4/2020 | B61B 1/00 |
| JP | 2009-015596 | A | | 1/2009 | |
| JP | 2010-211510 | A | | 9/2010 | |
| JP | 2011-166231 | A | | 8/2011 | |
| JP | 2017052578 | A | | 3/2017 | |
| JP | 2020063659 | A | | 4/2020 | |
| KR | 10-1988486 | B1 | | 6/2019 | |
| WO | 2019/031002 | A1 | | 2/2019 | |
| WO | 2020/044826 | A1 | | 3/2020 | |

OTHER PUBLICATIONS

Iketani, Tsubasa, "AI Measurements of Group Density, Video Analysis Solutions in Coronavirus Measures", MONOist, [online], May 11, 2020, [retrieved on Jun. 23, 2021], Internet <URL: https://web.archive.org/web/20200516035132/https://monoist.atmarkit.co.jp/mn/articles/2005/11/news043.html>, non-official translation.

Cristani et al., "The Visual Social Distancing Problem", arXiv.org, May 11, 2020, pp. 1-9, [online], [retrieved on Jun. 23, 2021], Internet <URL: https://arxiv.org/pdf/2005.04813.pdf>.

"Social Distancing Alert System Using Artificial Intelligence", Leeway Hertz, May 20, 2020, [online], [retrieved on Jun. 23, 2021], Internet <URL: https://web.archive.org/web/20200520075309/https://www.leewayhertz.com/social-distancing-alert-system-ai/>.

"Automated Social Distancing Detection helps your workplace reopen safely", Camio, Camiolog, Inc., May 20, 2020, [online], [retrieved on Jun. 23, 2021], Internet <URL: https://web.archive.org/web/20200520061113/https://www.camio.com/sd>.

JP Office Action for JP Application No. 2022-528471, mailed on Dec. 26, 2023 with English Translation.

* cited by examiner

FIG. 3

150

| IMAGE CAPTURING APPARATUS ID | • • • | |
|---|---|---|
| DATE AND TIME (FRAME NUMBER) | IMAGE DATA | ANALYSIS RESULT (INFECTION RISK INFORMATION) |
| • • • | • • • | • • • |
| • • • | • • • | • • • |
| • • • | • • • | • • • |
| • • • | • • • | • • • |

FIG. 20

150

152

| EVACUATION SITE ID | NUMBER OF ACCOMMODATED PERSONS | WHEELCHAIR | INFANT | ••• |
|---|---|---|---|---|
| EAST 2011 | 5000 | 1 | 0 | ••• |
| WEST 3008 | 300 | 0 | 1 | ••• |
| ••• | ••• | ••• | ••• | ••• |

IMAGE PROCESSING APPARATUS, IMAGE PROCESSING METHOD, AND NON-TRANSITORY COMPUTER-READABLE STORAGE MEDIUM

This application is a Continuation of U.S. application Ser. No. 18/007,969 filed on Dec. 2, 2022, which is a National Stage Entry of PCT/JP2021/015553 filed on Apr. 15, 2021, which claims priority from Japanese Patent Application 2020-098402 filed on Jun. 5, 2020, the contents of all of which are incorporated herein by reference, in their entirety.

TECHNICAL FIELD

The present invention relates to an image processing apparatus, an image processing method, and a program.

BACKGROUND ART

In recent years, image processing is used for various purposes. For example, Patent Document 1 describes a system that adjusts an environment within a space and brings an arrival range of a droplet from a first target person out of a respiratory area of a second target person, wherein a position and an orientation of a face of each of the first target person and second target person are determined by image processing.

RELATED DOCUMENT

Patent Document

Patent Document 1: International Patent Publication No. WO 2020/044826

SUMMARY OF INVENTION

Technical Problem

In order to reduce a risk of contracting an infectious disease, it is important to avoid a state where there is a possibility of contracting an infectious disease. However, since an appropriate action method for avoiding a state where there is a possibility of contracting an infectious disease is mostly not known to general public other than a specialist, an appropriate action may not be allowed, or a response may be delayed. One object of the present invention is to present an appropriate action method or execute an appropriate measure, for reducing a possibility of contracting an infectious disease in a place to be targeted.

Solution to Problem

The present invention provides an image processing apparatus including:

- an image processing unit that processes an image of a target region, and thereby computes a proximity index being an index relating to a proximity state of a plurality of persons captured in the image; and
- a control unit that causes a predetermined apparatus to execute predetermined control, when the proximity index satisfies a criterion.

The present invention provides an image processing method including, performing, by a computer:

- image processing of processing an image of a target region, and thereby computing a proximity index being an index relating to a proximity state of a plurality of persons captured in the image; and
- control processing of causing a predetermined apparatus to execute predetermined control, when the proximity index satisfies a criterion.

The present invention provides a program causing a computer to include:

- an image processing function of processing an image of a target region, and thereby computing a proximity index being an index relating to a proximity state of a plurality of persons captured in the image; and
- a control function of causing a predetermined apparatus to execute predetermined control, when the proximity index satisfies a criterion.

Moreover, the present invention provides an image processing apparatus including:

- an image processing unit that processes an image capturing a person to be moved to or placed in a predetermined place, and thereby determines an attribute of the person captured in the image; and
- a control unit that causes an output apparatus to output information proposing, according to the determined attribute, at least one of movement and placement of the person in such a way that the predetermined place is brought into a predetermined state.

The present invention provides an image processing method including, performing, by a computer:

- image processing of processing an image capturing a person to be moved to or placed in a predetermined place, and thereby determining an attribute of the person captured in the image; and
- output control processing of causing an output apparatus to output information proposing, according to the determined attribute, at least one of movement and placement of the person in such a way that the predetermined place is brought into a predetermined state.

The present invention provides a program causing a computer to include:

- an image processing function of processing an image capturing a person to be moved to or placed in a predetermined place, and thereby determining an attribute of the person captured in the image; and
- a control function of causing an output apparatus to output information proposing, according to the determined attribute, at least one of movement and placement of the person in such a way that the predetermined place is brought into a predetermined state.

Advantageous Effects of Invention

According to the present invention, it becomes easy to recognize or execute a means for reducing a possibility of contracting an infectious disease in a place to be targeted.

BRIEF DESCRIPTION OF THE DRAWINGS

FIG. 3 is a diagram illustrating one example of information stored by a storage unit.

FIG. 20 is a diagram illustrating one example of information stored by the storage unit.

EXAMPLE EMBODIMENT

Hereinafter, an example embodiment of the present invention is described by use of the drawings. Note that, a similar component is assigned with a similar reference sign in all of the drawings, and description thereof is not included, as appropriate.

First Example Embodiment

Figure 1:
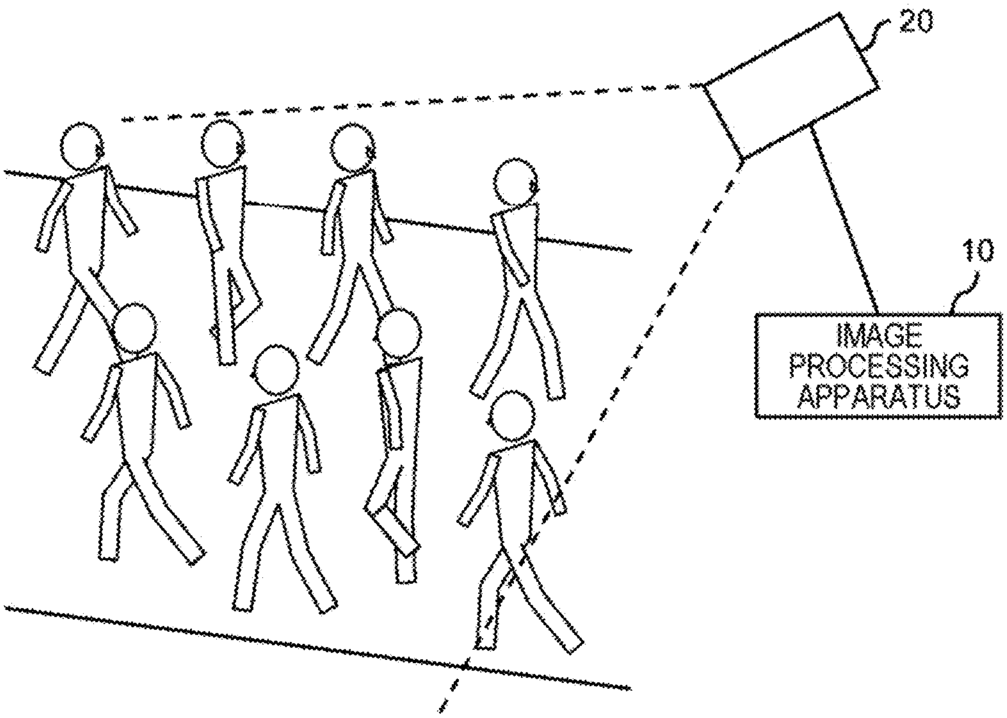
FIG. 1 is a diagram for describing a usage environment of an image processing apparatus according to an example embodiment.

FIG. 1 is a diagram for describing a usage environment of an image processing apparatus 10 according to an example embodiment. The image processing apparatus 10 is used together with an image capturing apparatus 20.

The image capturing apparatus 20 is, for example, a fixed camera, and repeatedly captures a region (hereinafter, referred to as a target region) where a plurality of persons, for example, an unspecified large number of persons come and go. Thus, an image generated by the image capturing apparatus 20 includes a plurality of persons. A frame rate of an image generated by the image capturing apparatus 20 is any frame rate, but may be, for example, such a frame rate as to make a moving image. Then, the image capturing apparatus 20 transmits the generated image to the image processing apparatus 10.

The image processing apparatus 10 processes an image generated by the image capturing apparatus 20, and thereby computes an interval between persons in a target region, i.e., a distance (hereinafter, referred to as a first distance) between a certain person (hereinafter, referred to as a criterial person) and a person being nearest to the certain person. Then, the image processing apparatus 10 generates, by use of the first distance, information (hereinafter, referred to as infection risk information) relating to a risk of contracting an infectious disease in a target region or a safety ratio of not contracting an infectious disease.

In an example illustrated in FIG. 1, the image processing apparatus 10 is connected to the one image capturing apparatus 20. However, the image processing apparatus 10 may be connected to a plurality of the image capturing apparatuses 20. In this case, the plurality of image capturing apparatuses 20 capture target regions differing from each other. Moreover, each of the plurality of image capturing apparatuses 20 transmits an image to outside in association with information (hereinafter, referred to as image capturing apparatus identification information) identifying the image capturing apparatus 20. In this way, infection risk information can be easily generated regarding each of a plurality of, for example, 100 or more large number of target regions.

Figure 2:
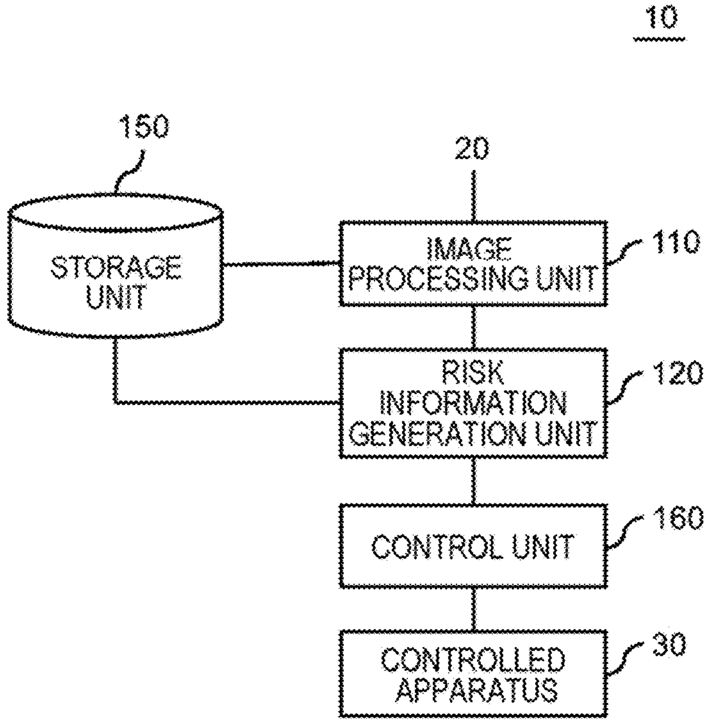
FIG. 2 is a diagram illustrating one example of a functional configuration of the image processing apparatus.

FIG. 2 is a diagram illustrating one example of a functional configuration of the image processing apparatus 10. The image processing apparatus 10 illustrated in the present figure includes an image processing unit 110, a risk information generation unit 120, and a control unit 160.

The image processing unit 110 acquires and processes an image generated by the image capturing apparatus 20, i.e., an image capturing a target region. As one example, the image processing unit 110 determines at least some of a plurality of persons captured in the image as the above-described criterial person, and computes the above-described first distance. A specific example of a computation method of a first distance is described later.

Further, the image processing unit 110 also performs other processing on the image as needed, and generates various pieces of information.

Note that, when the image processing apparatus 10 is connected to a plurality of the image capturing apparatuses 20, the image processing unit 110 acquires an image in association with image capturing apparatus identification information of the image capturing apparatus 20 that has generated the image.

The risk information generation unit 120 computes a proximity index being an index relating to a proximity state of a plurality of persons captured in an image. Then, the control unit 160 causes a predetermined apparatus to execute predetermined control, when the proximity index satisfies a criterion.

One example of a proximity index is, for example, exactly a risk of contracting an infectious disease in a target region or a safety ratio of not contracting an infectious disease, as described later. The risk or safety ratio is indicated by, for example, infection risk information generated by the risk information generation unit 120. A specific example of infection risk information is described later. Herein, "a criterion of a proximity index" is a criterion for detecting at least one of, for example, a situation where a risk of contracting an infectious disease is heightened, a situation where a sign of heightening of a risk is detected, and a situation where an action for avoiding a risk of contracting an infectious disease is necessary. Alternatively, "a criterion of a proximity index" is also a criterion for detecting at least one of a situation where a safety ratio of not contracting an infectious disease is decreasing, a situation where a sign of decrease of a safety ratio of not contracting an infectious disease is detected, and a situation where an action for heightening a safety ratio of not contracting an infectious disease is needed.

A predetermined apparatus refers to various controlled apparatuses 30 to be a target on which predetermined control is executed. A proximity state of persons can be eliminated within a target region by controlling the controlled apparatus 30. Various controlled apparatuses 30 can be conceived, and are exemplified by, but not limited to, the following.

(Apparatus example 1) At least one of an entrance gate and an exit gate of a target region (Apparatus example 2) A display apparatus such as an electric bulletin board or a liquid crystal display within a target region (Apparatus example 3) A self cash register or a semi-self cash register of a store (target region)

(Apparatus example 4) An automatic ticket machine in a station yard, a movie theater, a theater, an amusement park, a museum, an aquarium, a tourist facility, a restaurant, or the like (target region), a check-in reception machine in an airport (target region), an automatic reception machine or an automatic accounting machine in a hospital (target region), or a game machine in an amusement place such as an amusement arcade, a pinball parlor, or the like (target region)

(Apparatus example 5) A display apparatus for a manager of a target region

A target region is exemplified by, but not limited to, a shopping mall, an airport (a safety inspection area, a boarding waiting room, a lounge, a tenant, an observatory, and the like), a station (a place around a ticket machine, a place around a ticket gate, a yard (including a platform and a passage), and the like), a hospital (a waiting room, an accounting place, a hall, a passage, and the like), a store, a movie theater, a theater, an amusement park, a museum, an aquarium, a tourist facility, a temple, a library, a cram school, a public facility (a public office and the like), a restaurant within a facility, an eating and drinking place, a bank, an amusement place such as an amusement arcade or a pinball parlor, a gym, a gymnasium, a school (a classroom, a passage, and the like), an office (a workplace, a meeting room, a hall, a passage, and the like), a factory, a laboratory, and the like.

The risk information generation unit 120 generates, by use of the first distance, infection risk information in a target region determined as a capture target of the image capturing apparatus 20. As one example, the risk information generation unit 120 determines whether the first distance is equal to or less than a criterion value, and generates infection risk information by use of a result of the determination. The criterion value is determined based on a so-called social distance. The social distance is a physical distance that should be kept between adjacent persons, in order to prevent infection of an infectious disease. Then, magnitude of the criterion value is set based on a main infection route of a targeted infectious disease. For example, a value being equal to or more than 1.5 m and equal to or less than 6 m is used for a criterion value of an infectious disease mainly including droplet infection. Moreover, a value being equal to or more than 50 cm and equal to or less than 1.5 m is used for a criterion value of an infectious disease mainly including contact infection.

Note that, infection risk information indicates, for example, exactly a risk of contracting an infectious disease in a target region or a safety ratio of not contracting an infectious disease. In this case, as methods of generating infection risk information from the result of the determination described above, there are, for example, methods below.

(Method 1) The risk information generation unit 120 computes, for each image, the number of combinations of persons for whom a first distance is equal to or less than a criterion value, and heightens a risk indicated by infection risk information, as the number increases. When the method is used, the risk information generation unit 120 can generate infection risk information for each image.

(Method 2) The risk information generation unit 120 computes a per-unit-time occurrence amount of a combination of persons for whom a first distance is equal to or less than a criterion value, and heightens a risk indicated by infection risk information, as the occurrence amount increases. In this method, the risk information generation unit 120 uses processing results of a plurality of images generated at differing timings.

(Method 3) In Method 2, the risk information generation unit 120 uses per-unit-time and per-unit-area occurrence amounts.

Note that, in each of the methods described above, the image processing unit 110 can compute a time in which a state where a first distance is equal to or less than a criterion value continues, by processing a plurality of images being successive in terms of time. The risk information generation unit 120 may heighten a risk indicated by infection risk information, as a length of the time of continuation increases.

Note that, there is also a method of generating infection risk information without using a first distance. For example, the risk information generation unit 120 may compute per-unit-area density of persons in a target region, and heighten a risk indicated by infection risk information, as the density increases.

Moreover, the risk information generation unit 120 may use, as infection risk information, exactly a fact that a first distance is equal to or less than a criterion value.

Moreover, the image processing unit 110 stores, in a storage unit 150, an image generated by the image capturing apparatus 20. Herein, the image processing unit 110 may store, in the storage unit 150, information generated by processing an image, in association with the image. Note that, in the example illustrated in the present figure, the storage unit 150 serves as a part of the image processing apparatus 10. However, the storage unit 150 may be an external apparatus of the image processing apparatus 10.

The image processing unit 110 may generate the information described above, by processing an image stored in the storage unit 150. In this case, an image generated by the image capturing apparatus 20 can be temporarily stored in the storage unit 150, then read from the storage unit 150 at a desired timing, and processed. Note that, regardless of presence or absence of the storage unit 150, the image processing unit 110 can acquire, from the image capturing apparatus 20, an image generated by the image capturing apparatus 20, and process the image in real time.

FIG. 3 is a diagram illustrating one example of information stored by the storage unit 150. In the example illustrated in the present figure, the storage unit 150 stores an image (referred to as image data in FIG. 3) generated by the image capturing apparatus 20, in association with information (e.g., exactly a date and time or a frame number) determining the date and time when the image is generated. Moreover, the storage unit 150 stores an image generated by the image capturing apparatus 20, together with information (referred to as an analysis result in FIG. 3) acquired by processing the image. Note that, the analysis result may include infection risk information.

Figure 4:
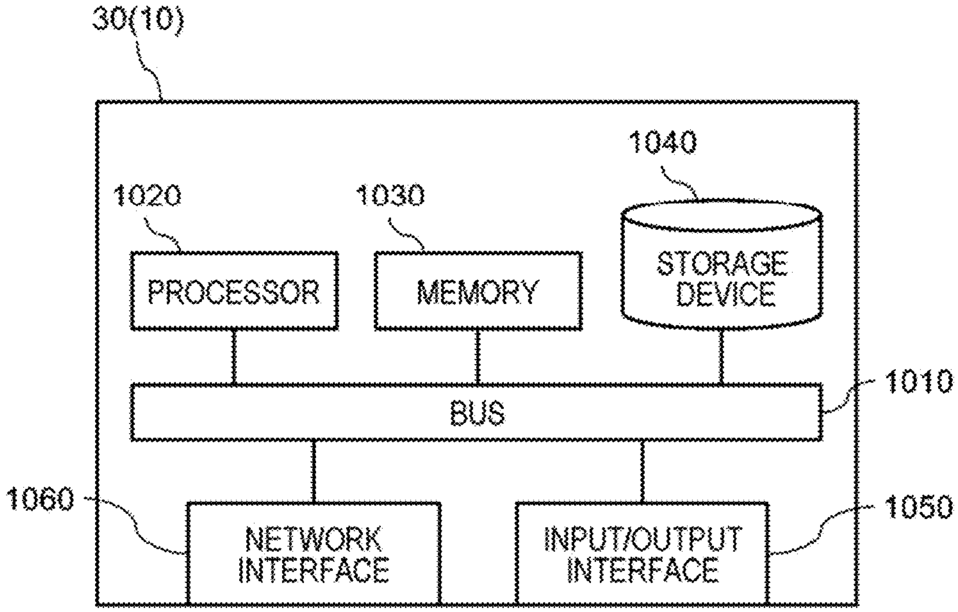
FIG. 4 is a diagram illustrating a hardware configuration example of the image processing apparatus.

FIG. 4 is a diagram illustrating a hardware configuration example of the image processing apparatus 10. The image processing apparatus 10 includes a bus 1010, a processor 1020, a memory 1030, a storage device 1040, an input/output interface 1050, and a network interface 1060.

The bus 1010 is a data transmission path through which the processor 1020, the memory 1030, the storage device 1040, the input/output interface 1050, and the network interface 1060 transmit/receive data to/from one another. However, a method of mutually connecting the processor 1020 and the like is not limited to bus connection.

The processor 1020 is a processor achieved by a central processing unit (CPU), a graphics processing unit (GPU), or the like.

The memory 1030 is a main storage apparatus achieved by a random access memory (RAM) or the like.

The storage device 1040 is an auxiliary storage apparatus achieved by a hard disk drive (HDD), a solid state drive (SSD), a memory card, a read only memory (ROM), or the like. The storage device 1040 stores a program module that achieves each function (e.g., the image processing unit 110, the risk information generation unit 120, the control unit 160, and an attribute determination unit 170) of the image processing apparatus 10. The processor 1020 reads each of the program modules onto the memory 1030, executes the read program module, and thereby achieves each function being associated with the program module. Moreover, the storage device 1040 may also function as the storage unit 150.

The input/output interface 1050 is an interface for connecting the image processing apparatus 10 and various pieces of input/output equipment with each other.

The network interface 1060 is an interface for connecting the image processing apparatus 10 to a network. The network is, for example, a local area network (LAN) or a wide area network (WAN). A method of connecting the network interface 1060 to a network may be wireless connection or may be wired connection. The image processing apparatus 10 may communicate with the image capturing apparatus 20 via the network interface 1060.

Figure 5:
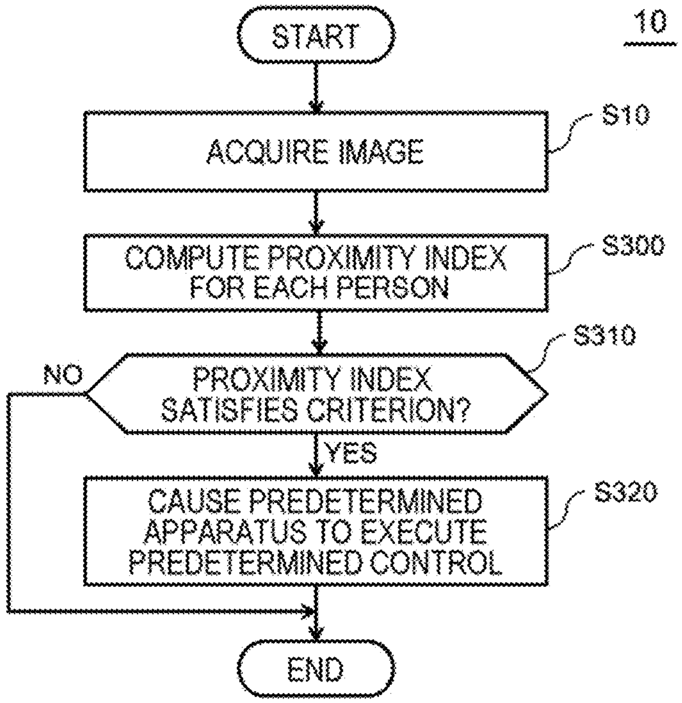
FIG. 5 is a flowchart illustrating a first example of processing to be performed by the image processing apparatus.

FIG. 5 is a flowchart illustrating a first example of processing to be performed by the image processing apparatus 10. First, the image processing unit 110 of the image processing apparatus 10 acquires an image to be a processing target (step S10). An image of a processing target is an image of a target region. At least one person is captured in the image. Then, the risk information generation unit 120 processes the image, and computes an index relating to a proximity state of a plurality of persons included in the image (step S300). In the computation, the image processing unit 110 computes a first distance by use of a height and a position, within an image, of a person targeted for computation of a distance, and an orientation in an up-down direction of the image capturing apparatus 20 that has generated the image. In this instance, as details are described later, the image processing unit 110 uses a value (hereinafter, referred to as a criterion height) previously set as a height of a person.

Next, the control unit 160 determines whether the proximity index generated in step S300 satisfies a criterion (step S310). When the proximity index satisfies the criterion (YES in step S310), the control unit 160 causes the controlled apparatus 30 to execute predetermined control (step S320). Namely, the control unit 160 detects a situation where a proximity state of persons within a target region is becoming dense, and a risk of contracting an infectious disease is heightened, or a situation where a safety ratio of not contracting an infectious disease is decreasing, and causes the controlled apparatus 30 to execute predetermined control. The processing in step S320 causes the various controlled apparatuses 30 to execute a measure for easing a proximity state in a target region, as details are described later, and differs according to a characteristic of a target region.

On the other hand, when the proximity index does not satisfy the criterion (NO in step S310), step S320 is bypassed, and the present processing is finished. Namely, persons within the target region are not in a dense state, but in a situation where a risk of contracting an infectious disease is not heightened, or a situation where a safety ratio of not contracting an infectious disease is not decreasing, it is determined that a measure for easing a proximity state does not need to be performed.

Various control methods for the controlled apparatus 30 to be performed in step S320 in FIG. 5 can be conceived, and are exemplified by, but not limited to, the following.

Control Example 1

In this example, the controlled apparatus 30 is the (Apparatus example 1) described above, and is, for example, an entrance gate to a target region. Then, when a proximity index satisfies a criterion (YES in step S310), the control unit 160 closes the entrance gate, and limits entrance (step S320). In this example, a target region is exemplified by, but not limited to, for example, a station, a safety inspection area of an airport, a hospital, a facility, a store, an amusement park, an amusement place, a bank, an office building, a factory, and a library. A target region may be a region further divided within each of the facilities, for example, in a case of a hospital, each of divided regions such as a reception floor, a consultation waiting room, a test waiting floor, an accounting floor, and a passage. The control unit 160 may control an entrance gate that limits entrance into each division.

Control Example 2

In this example, the controlled apparatus 30 is the (Apparatus example 1) described above, and is, for example, an entrance gate and an exit gate provided for a person to enter and exit from a target region. Herein, entrance gates and exit gates are provided in a plurality of places. It is assumed that at least one of the entrance gates and the exit gates provided in a plurality of places has a limit in utilization time. Then, when a proximity index satisfies a criterion (YES in step S310), the control unit 160 changes the limited utilization time (step S320). A change of a utilization time refers to prolonging or shifting a limited utilization time. The processing increases the number of gates that can be utilized by a person to enter and exit from a target region, thereby spreads a person flow, eliminates a stagnancy in person flow during entrance and exit, and eases a proximity state. In this example as well as in the (Control example 1) described above, a target region is exemplified by, but not limited to, for example, a station, a safety inspection area of an airport, a hospital, a facility, a store, an amusement park, an amusement place, a bank, an office building, a factory, a library, and the like.

Control Example 3

In this example, the controlled apparatus 30 is the (Apparatus example 3) and (Apparatus example 4) described above, and is, for example, a self cash register or a semi-self cash register of a store (target region), an automatic ticket machine in a station yard or the like (target region), a check-in reception machine in an airport (target region), an automatic reception machine or an automatic accounting machine in a hospital (target region), or the like. A plurality of the apparatuses are installed in a target region. Then, when a proximity index satisfies a criterion (YES in step S310), the control unit 160 activates the deactivated controlled apparatus 30 (step S320). The control unit 160 may instruct a control unit of the controlled apparatus 30 to activate the controlled apparatus 30, or may instruct a power switch apparatus of the controlled apparatus 30 to apply a power supply.

In this example, when a proximity index of a target region satisfies a criterion, a waiting time can be shortened by increasing the number of the activated controlled apparatuses 30 relating to a person in the target region, and a stay time of a person within the target region can be shortened.

Control Example 4

In this example, the controlled apparatus 30 is the (Apparatus example 2) described above, and is, for example, a display apparatus such as an electric bulletin board or a liquid crystal display within a target region. Then, when a proximity index satisfies a criterion (YES in step S310), the control unit 160 displays, on a display apparatus, information guiding from the target region to another place, information urging to exit from the target region, or the like (step S320). In this example as well as in the (Control example 1) described above, a target region is exemplified by, but not limited to, for example, a station, a safety inspection area of an airport, a hospital, a facility, a store, an amusement park, an amusement place, a bank, an office building, a factory, a library, and the like.

Control Example 5

In this example, the controlled apparatus 30 is the (Apparatus example 5) described above, and is, for example, a display apparatus for a manager of a target region. The manager is not a manager as a post, and may be a person who substantially manages the place. In other words, the manager is a person who performs a measure for easing a proximity state of a target region (being one example of a predetermined state), according to information output to the display apparatus. Then, when a proximity index satisfies a criterion (YES in step S310), the control unit 160 causes a display apparatus to display measure information indicating a measure for easing a proximity state of a target region (being one example of a predetermined state) (step S320). In this example as well as in the (Control example 1) described above, a target region is exemplified by, but not limited to, for example, a station, a safety inspection area of an airport, a hospital, a facility, a store, an amusement park, an amusement place, a bank, an office building, a factory, a library, and the like.

Various measure examples to be indicated in measure information can be conceived, and are exemplified by, but not limited to, the following.

(Measure example 1) Instruct to increase and place a clerk at a manned cash register of a store (target region).

(Measure example 2) Instruct to increase and place a clerk at a window in a safety inspection area (target region) of an airport.

(Measure example 3) Instruct to guide into a target region or place a guide staff.

(Measure example 4) Instruct to perform entrance regulation to a target region (e.g., a station yard, a store, or the like). Alternatively, inform at least one of a manager and a user of a target region, of a date and time when entrance regulation should be performed.

(Measure example 5) Instruct to increase the number of the controlled apparatuses 30 within a target region.

Figure 6:
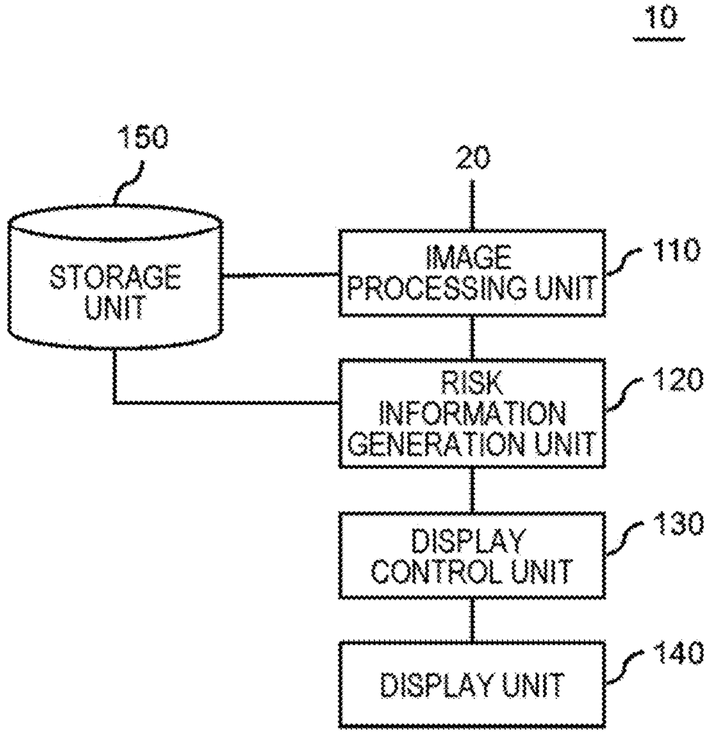
FIG. 6 is a diagram illustrating one example of a functional configuration of the image processing apparatus.

A case where the controlled apparatus 30 is a display apparatus is described below. FIG. 6 is a diagram illustrating one example of a functional configuration of the image processing apparatus 10. The image processing apparatus 10 illustrated in the present figure includes a display control unit 130 in place of the control unit 160 in FIG. 2. Moreover, the image processing apparatus 10 targets a display unit 140 for control as an example of the controlled apparatus 30 in FIG. 2. In this example, the display control unit 130 superposes, on an image determined as a processing target, display for causing to recognize a combination of persons for whom a first distance is equal to or less than a criterion value, i.e., a combination of a criterial person and a person being nearest to the criterial person, and then displays the display and the image on the display unit 140. The display unit 140 includes a display. In the example illustrated in the present figure, the display unit 140 is a part of the image processing apparatus 10, but may be present outside the image processing apparatus 10. The display unit 140 may also include the (Apparatus example 2) and (Apparatus example 5) described above.

Figure 7:
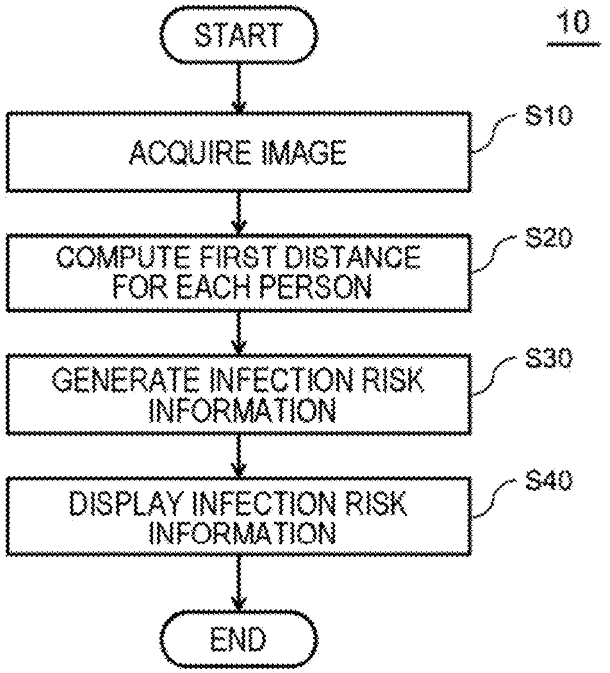
FIG. 7 is a flowchart illustrating a second example of processing to be performed by the image processing apparatus.

FIG. 7 is a flowchart illustrating a second example of processing of the risk information generation unit 120. The processing may be executed in parallel with the processing in FIG. 5. First, the image processing unit 110 of the image processing apparatus 10 acquires an image to be a processing target (step S10). Then, the image processing unit 110 processes the image, and computes the first distance described above, for each person included in the image (step S20). In the computation, the image processing unit 110 computes the first distance by use of a height and a position, within an image, of a person targeted for computation of a distance, and an orientation in an up-down direction of the image capturing apparatus 20 that has generated the image. In this instance, as details are described later, the image processing unit 110 uses a value (hereinafter, referred to as a criterion height) previously set as a height of a person.

Next, the risk information generation unit 120 generates infection risk information by use of the first distance generated in step S20. An example of a generation method of infection risk information is as described by use of FIG. 2 (step S30). Then, the display control unit 130 displays the generated infection risk information on the display unit 140 (step S40). In this instance, the display control unit 130 may display, together with the infection risk information, an image (a moving image in some cases) used when the infection risk information is generated (step S40). An example of an image displayed herein is described later.

Figure 8:
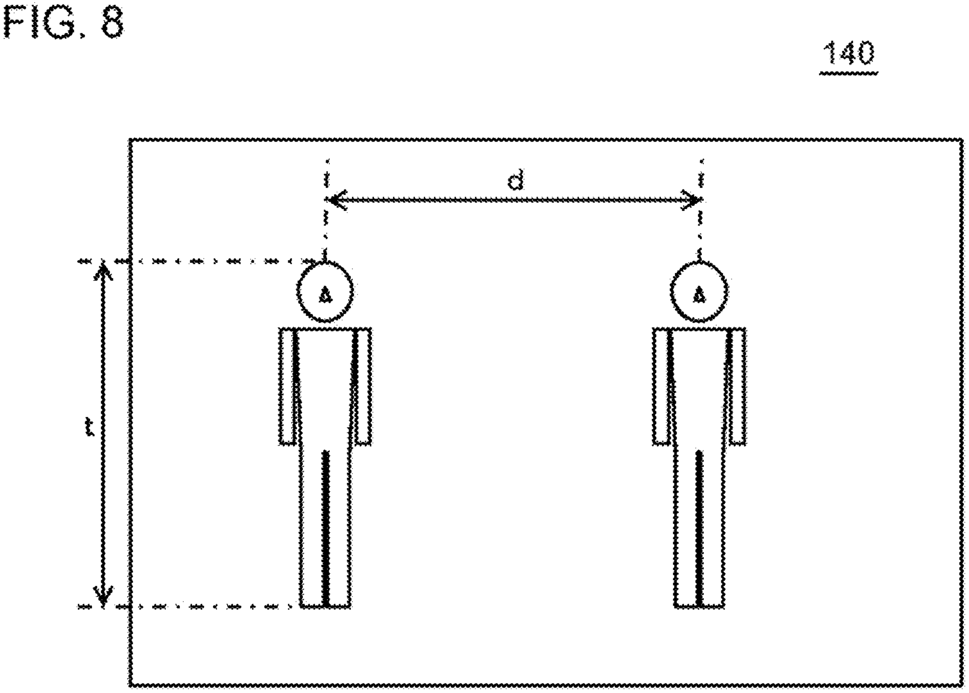
FIG. 8 is a diagram illustrating one example of a computation method of a first distance performed in step S20 in FIG. 7.

FIG. 8 is a diagram illustrating one example of a computation method of a first distance performed in step S20 in FIG. 7. The image processing unit 110 determines a criterial person. Then, processing illustrated in the present figure is performed for each of persons positioned around the criterial person.

First, the image processing unit 110 computes a height t, in an image, of a criterial person, or a person positioned around the criterial person. Herein, for example, t is represented by the number of pixels. Next, the image processing unit 110 computes a distance d within an image from the criterial person to the person positioned therearound. Herein, d is represented by the same unit (e.g., the number of pixels) as t. Next, the image processing unit 110 computes d/t, multiplies the value d/t by the criterion length described above, and thereby computes a distance between the criterial person and the person positioned therearound.

When there is only one person around other than a criterial person, a distance computed regarding the person becomes a first distance. Moreover, when there are a plurality of other persons, the distance described above is computed regarding each of the plurality of persons, and a minimum value of the distance becomes a first distance.

Note that, as described above, a criterion height is previously set. The criterion height may be varied depending on a place (e.g., a country) where the image capturing apparatus 20 is installed. For example, an average height of an adult in a country where the targeted image capturing apparatus 20 is installed is used for a criterion height. As an example of specific processing, the storage unit 150 stores, for each piece of image capturing apparatus identification information, information that determines a criterion height. Then, the image processing unit 110 acquires image capturing apparatus identification information of the image capturing apparatus 20 that has generated an image targeted for processing, reads a criterion height being associated with the image capturing apparatus identification information from the storage unit 150, and uses the read criterion height.

Moreover, when an attribute (e.g., at least one of gender or an age group) of a person targeted for computation of the height t can be estimated by image processing, the image processing unit 110 may change the criterion height by the attribute.

Note that, in most images, distortion specific to the image capturing apparatus 20 that has generated the image has occurred. When computing a first distance, the image processing unit 110 preferably performs processing of correcting the distortion. The image processing unit 110 performs distortion correction processing according to a position of a person within an image. Generally, distortion of an image results from, for example, an optical system (e.g., a lens) included in the image capturing apparatus 20, and an orientation in an up-down direction (e.g., an angle to a horizontal plane) of the image capturing apparatus 20. Accordingly, a content of distortion correction processing according to a position of a person within an image is set according to an optical system (e.g., a lens) included in the image capturing apparatus 20, and an orientation in an up-down direction of the image capturing apparatus 20.

Note that, in the processing described by use of the present figure, when an image includes an object a size of which is standardized to a certain degree, the image processing unit 110 may compute a first distance by use of the size of the object instead of a height of a person.

Figure 9:
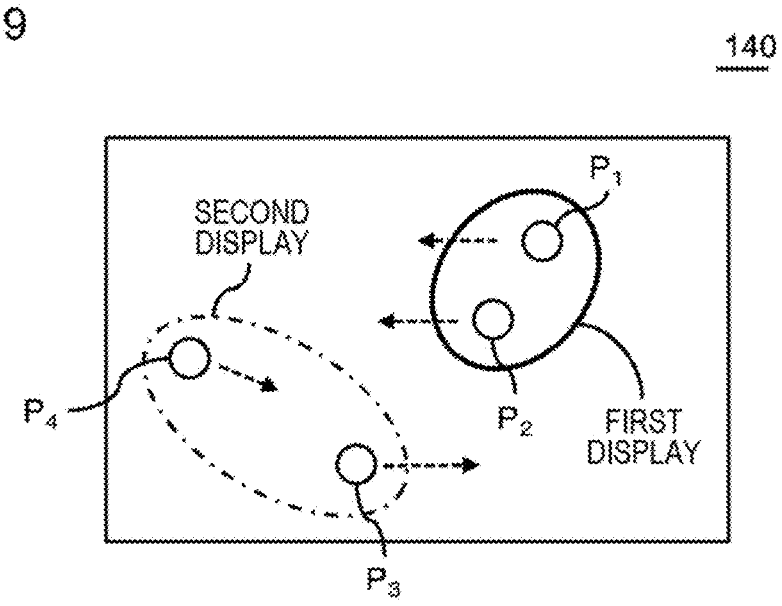
FIG. 9 is a diagram illustrating a first example of an image displayed on a display unit in step S40 in FIG. 7.

FIG. 9 is a diagram illustrating a first example of an image displayed on the display unit 140 in step S40 in FIG. 7. The display control unit 130 causes the display unit 140 to display, together with infection risk information, an image (a moving image in some cases) used when the infection risk information is generated. In the example illustrated in the present figure, the display control unit 130 superposes, on an image, display for causing to recognize a combination of persons for whom a first distance is equal to or less than a criterion value, and then causes the display unit 140 to display the display and the image.

As one example, the display control unit 130 causes the display unit 140 to display a mark indicating a combination of persons recognized by the image processing unit 110. Then, the display control unit 130 varies an aspect of the mark by whether a first distance is equal to or less than a criterion value. More specifically, in the example illustrated in the present figure, two persons constituting a combination of persons are surrounded with a circle or an ellipse. Then, a display color of the circle or ellipse and an aspect of a line (a full line, a dotted line, a one-dot chain line, and the like) vary by whether a first distance is equal to or less than a criterion value.

Figure 10:
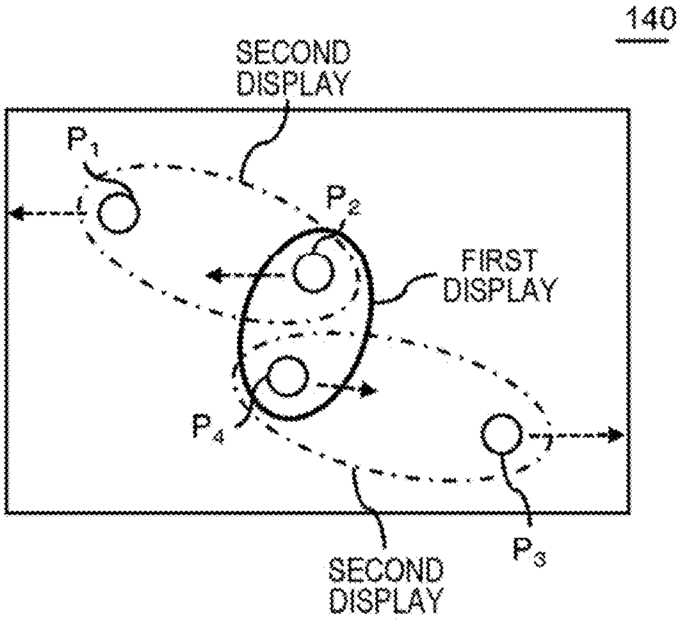
FIG. 10 is a diagram illustrating the first example of an image displayed on the display unit in step S40 in FIG. 7.

Note that, when an image to be displayed is a moving image, a combination of persons to be a computation target of a first distance varies as time elapses, as illustrated in FIGS. 9 and 10. For example, at a timing in FIG. 9, a person P1 is a partner for a person P2 when a first distance is computed, but, at a later timing in FIG. 10, a person P4 is a partner when a first distance is computed.

Figure 23:
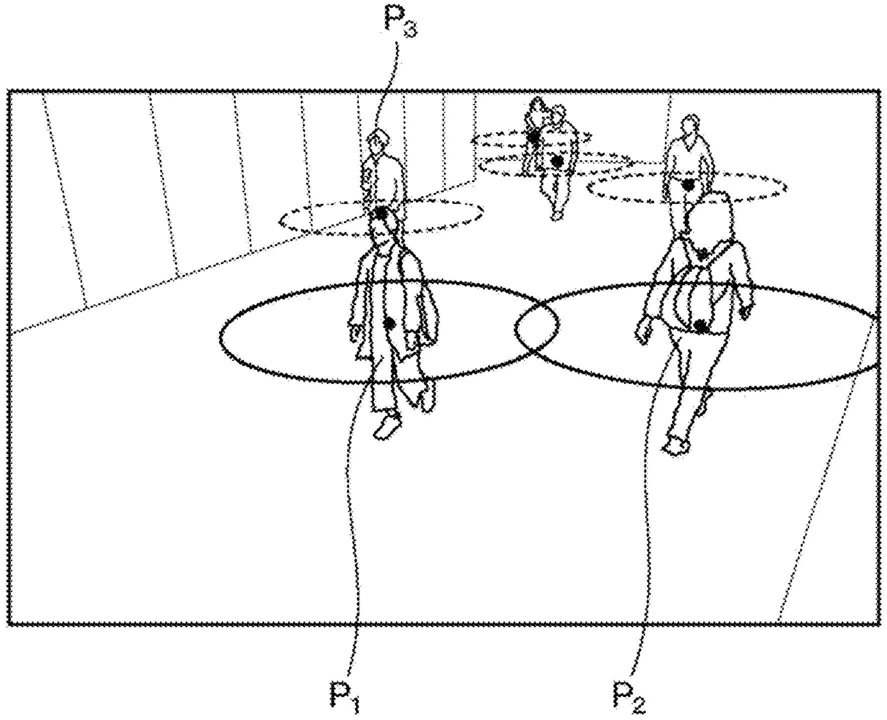
FIG. 23 is a diagram illustrating a second example of an image displayed on the display unit in step S40 in FIG. 7.
Figure 24:
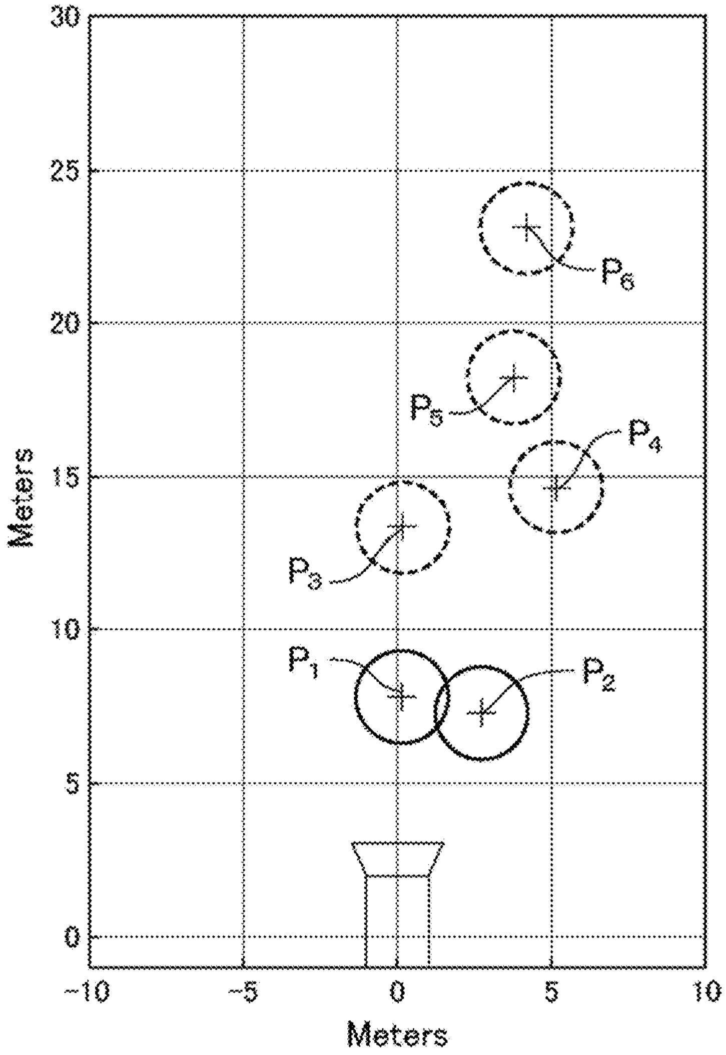
FIG. 24 is a diagram illustrating the second example of an image displayed on the display unit in step S40 in FIG. 7.

Each of FIGS. 23 and 24 is a diagram illustrating a second example of an image displayed on the display unit 140 in step S40 in FIG. 7. In each of the figures, the display control unit 130 displays, for each person, a mark indicating a range of a recommended value (e.g., the criterion value described above) of a social distance around the person. Then, when a mark being associated with a certain person overlaps a mark being associated with a person being near the certain person, i.e., when a distance between a certain person and a person being near the certain person becomes equal to or less than a recommended value of a social distance (e.g., the persons P1 and P2 in FIGS. 23 and 24), the mark being associated with each of the two persons is displayed in an aspect differing from that of the mark (e.g., a person P3 in FIG. 23, and persons P3, P4, P5, and P6 in FIG. 24) being associated with another person. A way of causing an aspect to differ is, for example, varying a display color, causing an aspect of a line (a full line, a dotted line, a one-dot chain line, and the like) constituting a mark to differ, or the like. The display control unit 130 displays, when varying a display color, a mark of, for example, a normal state in blue, or displays, when two marks overlap each other, the two marks in red.

In the example illustrated in FIG. 23, the display control unit 130 superposes the mark described above on an image (a moving image in some cases) used when the infection risk information is generated. On the other hand, in the example illustrated in FIG. 24, placement of a person is indicated with a plan view, and then, the mark described above is superposed on the plan view. The display control unit 130 may cause the display unit 140 to simultaneously display the display illustrated in FIG. 23 and the display illustrated in FIG. 24.

Display illustrated in each of FIGS. 9, 10, 23, and 24 may be performed by use of a real-time moving image or image. In this case, the display illustrated in each of the figures may be performed on, for example, the display unit 140 installed near a target region, or may be used as contents of the Internet or broadcasting.

Figure 11:
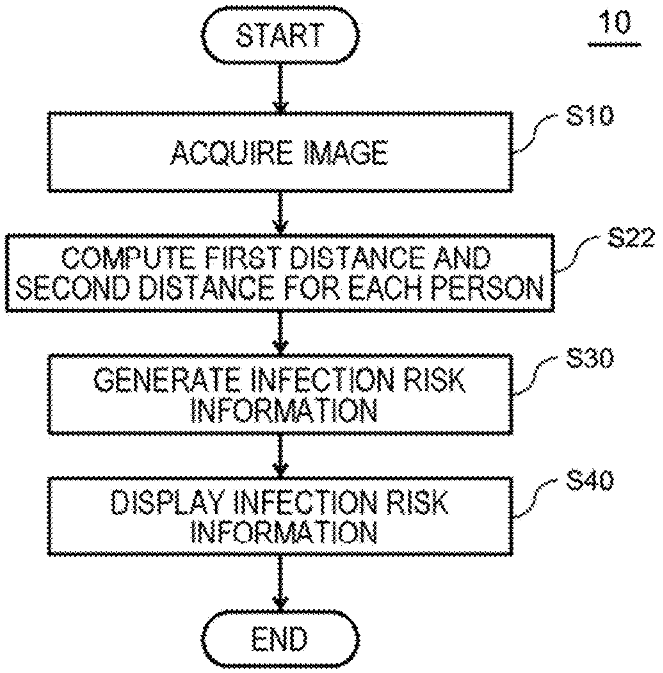
FIG. 11 is a flowchart illustrating a third example of processing to be performed by the image processing apparatus.

FIG. 11 is a flowchart illustrating a third example of processing to be performed by the image processing apparatus 10. The example illustrated in the present figure is similar to the example illustrated in FIG. 7 except that the image processing unit 110 computes a second distance as well when computing a first distance (step S22), and generates infection risk information further by use of the second distance (step S30).

The second distance is a distance between a criterial person and a person being second nearest from the criterial person. A computation method of the second distance is similar to a computation method of the first distance except that a distance to a person not being nearest but being second nearest is selected. Then, when generating infection risk information, the risk information generation unit 120 generates in such a way that a risk heightens (a safety ratio lowers) as the second distance shortens. Note that, the image processing unit 110 may further generate a distance (third distance) between a criterial person and a person being third nearest from the criterial person. In this case, the risk information generation unit 120 generates infection risk information further by use of the third distance.

Figure 12:
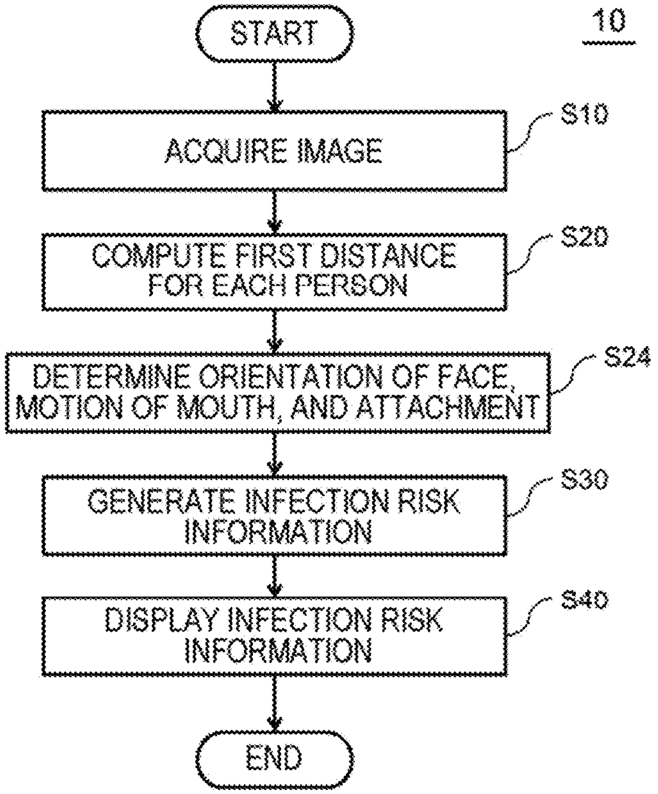
FIG. 12 is a flowchart illustrating a fourth example of processing to be performed by the image processing apparatus.

FIG. 12 is a flowchart illustrating a fourth example of processing to be performed by the image processing apparatus 10. The example illustrated in the present figure is similar to the example illustrated in FIG. 7 or 11 except that the risk information generation unit 120 further uses information other than a distance between persons when generating infection risk information.

To be specific, steps S10 and S20 (or S22) are similar to the example illustrated in FIG. 7 (or 11). Then, the image processing unit 110 processes an image, and thereby generates additional information necessary to generate infection risk information. Information generated herein is at least one of a determination result of an orientation of a face of a person, presence or absence of an attachment to a face and a determination result of a kind of the attachment, and a determination result of motion of a mouth of a person (step S24).

An "orientation of a face of a person" at least includes at least one of an orientation of a face of a criterial person, and an orientation of a face of a person being nearest to the criterial person. Then, the risk information generation unit 120 heightens a risk indicated by the infection risk information (lowers a safety ratio), as a face of a person becomes close in a direction facing a partner. Herein, when using a second distance or a third distance, the image processing unit 110 and the risk information generation unit 120 may further use an orientation of a face of a person to be a partner when the second distance is computed, or an orientation of a face of a person to be a partner when the third distance is computed.

"Presence or absence of an attachment to a face" at least includes at least one of presence or absence of an attachment in a criterial person, and presence or absence of an attachment in a person being nearest to the criterial person. Then, in a case where an attachment of a specific kind is sensed, the risk information generation unit 120 compares the case with other cases, and lowers a risk indicated by infection risk information (raises a safety ratio). Herein, an attachment of a specific kind is a cover of at least one (preferably both) of a mouth and a nose, for example, a mask or a muffler. Herein, when using a second distance or a third distance, the image processing unit 110 and the risk information generation unit 120 may further perform similarly for a person to be a partner when the second distance is computed, or a person to be a partner when the third distance is computed.

"Motion of a mouth" means that at least a mouth is moving. When a mouth is moving, there is a high possibility that the person is talking. Accordingly, in a case where a mouth is moving in at least one of a criterial person, and a person being nearest to the criterial person, the risk information generation unit 120 compares the case with other cases, and heightens a risk indicated by infection risk information (lowers a safety ratio). Herein, when using a second distance or a third distance, the image processing unit 110 and the risk information generation unit 120 may further use motion of a mouth of a person to be a partner when the second distance is computed, or motion of a mouth of a person to be a partner when the third distance is computed.

Figure 13:
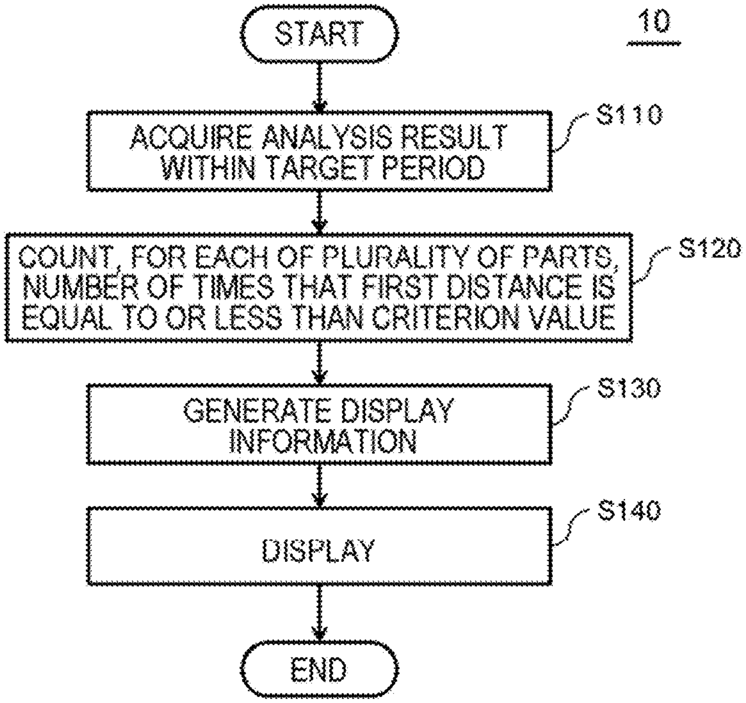
FIG. 13 is a flowchart illustrating a fifth example of processing to be performed by the image processing apparatus.

FIG. 13 is a flowchart illustrating a fifth example of processing to be performed by the image processing apparatus 10. The image processing apparatus 10 also performs processing illustrated in the present figure, in addition to the processing illustrated in FIG. 5, 7, 11, or 12.

In the example illustrated in the present figure, the image capturing apparatus 20 is a fixed camera. Thus, a specific position of a target region is associated with each position within an image. The image processing unit 110 previously stores a relation of the association. As described above, the risk information generation unit 120 computes a proximity index being an index relating to a proximity state of a plurality of persons. When the proximity index satisfies a criterion, the control unit 160 causes the controlled apparatus 30 to execute predetermined control.

More specifically, the image processing unit 110 of the image processing apparatus 10 determines, in step S20 in FIGS. 7 and 12 or step S22 in FIG. 11, a position where a first distance within an image is equal to or less than a criterion value, and thereby determines a position where a first distance is equal to or less than a criterion value in a target region. Then, the image processing unit 110 stores, in the storage unit 150, information indicating the position, in association with the processed image.

Then, the risk information generation unit 120 of the image processing apparatus 10 processes the information stored in the storage unit 150, and thereby counts up, for each position within the target region, the number of times (one example of the proximity index described above) that a first distance is equal to or less than a criterion value in a target period. A length of the target period may be, for example, one day, one week, or one month.

Specifically, first, the risk information generation unit 120 acquires information that determines the image capturing apparatus 20 to be a target, and information that determines a start and an end of a target period. The acquisition is performed by, for example, being input from a user. Next, the risk information generation unit 120 reads, from the storage unit 150, an analysis result of an image generated in a target period by the image capturing apparatus 20 to be a target. Information read herein includes information indicating a position where a first distance is equal to or less than a criterion value. The information is generated for each image (step S110).

Moreover, the target region is previously separated into a plurality of parts. Then, the risk information generation unit 120 counts, for each of the plurality of parts, the number of times that a first distance is equal to or less than a criterion value (step S120). Note that, the above-described "position where a first distance is equal to or less than a criterion value" in the information stored in the storage unit 150 may be information indicating the part.

Then, the risk information generation unit 120 outputs information indicating a part where the number of counts is equal to or more than a criterion value. The part indicating by the information is a part where an infection risk is high, i.e., a place needing care. In the example illustrated in the present figure, the risk information generation unit 120 outputs information indicating the part. A destination of the output is, for example, the display control unit 130. In this case, the display control unit 130 generates display information for displaying information indicated by the part (step S130), and causes the display unit 140 to display the display information (step S140).

As described by use of FIG. 6, the image processing unit 110 can compute a time in which a state where a first distance is equal to or less than a criterion value continues, by processing a plurality of images being successive in terms of time. In this case, the image processing unit 110 may perform the processing described above, by counting the number of times that a state where a first distance is equal to or less than a criterion value continues for equal to or more than a criterion time.

Moreover, output performed by the risk information generation unit 120 is used to determine a place where persons tend to crowd together within a target region, and improve such a place (e.g., improve a person flow). As one example, when a target region is inside a building, the output is used as reference data for changing arrangement or the number of objects (e.g., benches in a waiting room) arranged inside the building (e.g., a waiting room or a corridor). Note that, a flow to be an improvement target includes, for example, a flow from a waiting room to a consultation room within a hospital, and a flow from an entrance to a treatment room in a hospital.

Herein, a facility such as a hospital, a public office, a station, and an airport is cited as an example of inside a building, but inside a building may be a store, for example, a large store (including a case of being attached to an airport or a station) such as a shopping mall. In the latter case, output performed by the risk information generation unit 120 determines a place where persons tend to crowd together within a building being a large store. Then, a result of the determination is used as reference data when arrangement and a flow of a tenant are changed in such a way that persons do not crowd together in the place.

In the example described above, a unit when setting a "place needing care" is set by dividing one target region into a plurality of parts. On the other hand, a plurality of image capturing apparatuses 20 may be connected to the image processing apparatus 10, and the plurality of image capturing apparatuses 20 may capture places of the same facility differing from each other. In this case, a unit when setting a "place needing care" may be a capture region (i.e., one target region) of one image capturing apparatus 20. To this end, the image processing unit 110 may count, not for each of the plurality of parts described above but for each of the image capturing apparatuses 20, the number of times that a first distance is equal to or less than a criterion value, or the number of times that this state continues for equal to or more than a criterion time.

Figure 14:
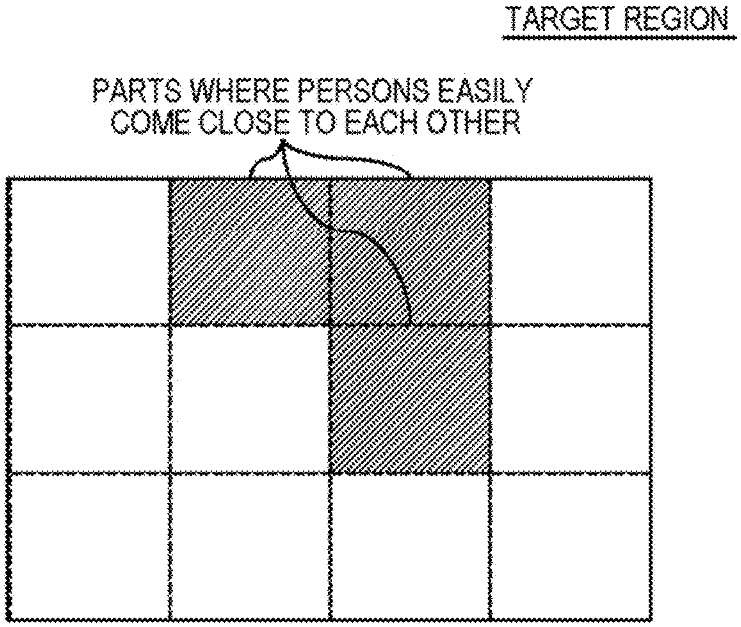
FIG. 14 illustrates one example of a screen displayed on the display unit in step S140 in FIG. 13.

FIG. 14 illustrates one example of a screen displayed on the display unit 140 in step S140 in FIG. 13. In the example illustrated in the present figure, the display unit 140 displays a plan view of a target region. Then, the display control unit 130 causes the display unit 140 to display, identifiably from other parts, a part of the plan view where the number of counts in step S120 is equal to or more than a criterion value.

Note that, a plurality of values may be set stepwise as criterion values relating to the number of counts. In this case, the risk information generation unit 120 determines which value among the criterion values the number of counts in step S120 has exceeded, and outputs information indicating the determined value. For example, depending on the output, the display control unit 130 may vary a display aspect of the part. For example, a part exceeding only the lowest criterion value may be indicated in green, and a part exceeding the highest criterion value may be indicated in red.

Figure 15:
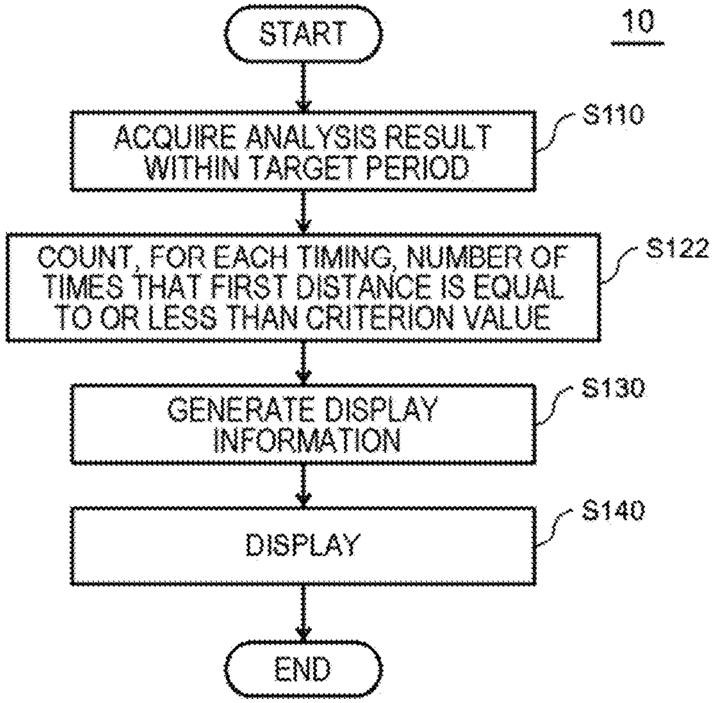
FIG. 15 is a flowchart illustrating a sixth example of processing to be performed by the image processing apparatus.

FIG. 15 is a flowchart illustrating a sixth example of processing to be performed by the image processing apparatus 10. The image processing apparatus 10 also performs processing illustrated in the present figure, in addition to the processing illustrated in FIG. 5, 7, 11, or 12. Moreover, the image processing apparatus 10 may also further perform the processing illustrated in FIG. 13.

In the present figure, the risk information generation unit 120 of the image processing apparatus 10 determines a timing when a risk of contracting an infectious disease is heightened (a timing when a safety ratio lowers). The timing is set, for example, for each day of a week, each time period, or each day of a week and each time period.

In the example illustrated in the present figure, processing illustrated in step S110 is similar to the processing described by use of FIG. 13.

Next, the risk information generation unit 120 counts, for each timing, the number of times that a first distance is equal to or less than a criterion value (step S122). Herein, the risk information generation unit 120 may further perform counting for each timing, for each of a plurality of parts within a target region, as illustrated in FIG. 13.

Next, the risk information generation unit 120 outputs information indicating a timing when the number of counts is equal to or more than a criterion value. A timing (e.g., a time period or a day of a week) indicated by the information is a timing when an infection risk is high. As one example, the risk information generation unit 120 outputs information indicating the timing to the display control unit 130. Accordingly, the display control unit 130 generates display information for displaying information indicating the timing (step S130), and causes the display unit 140 to display the display information (step S140).

Note that, when a target region is inside a store, the display unit 140 may be provided at an entrance or within a show window of the store. In this way, a person who is about to enter the store can recognize a timing when the store seems to be uncrowded. Moreover, the display control unit 130 may disclose, on the Internet, display information generated in step S130. In this way, a person who is about to go to the store can recognize a timing when the store seems to be uncrowded.

Moreover, when a target region is inside a store, and the display unit 140 is provided at an entrance or within a show window of the store, the display control unit 130 may cause the display unit 140 to display current infection risk information, or perform display illustrated in FIGS. 9, 10, 23, and 24 by use of a real-time moving image or image.

Figure 16:
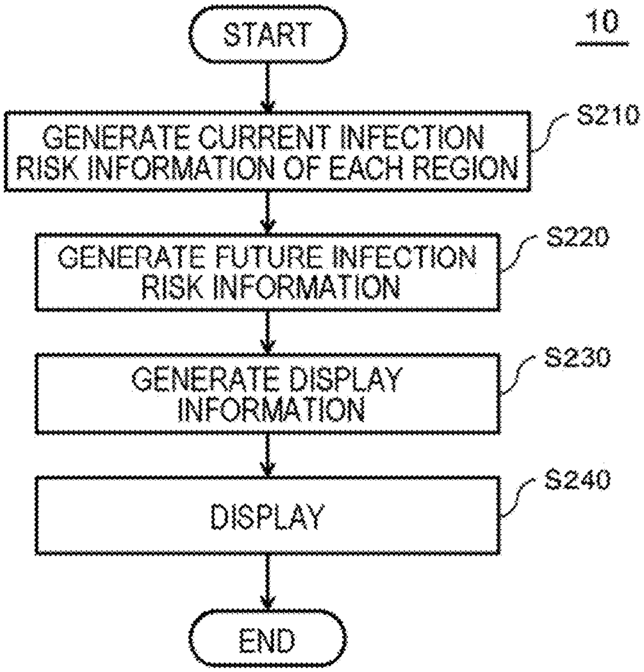
FIG. 16 is a flowchart illustrating a seventh example of processing to be performed by the image processing apparatus.

FIG. 16 is a flowchart illustrating a seventh example of processing to be performed by the image processing apparatus 10. The image processing apparatus 10 also performs processing illustrated in the present figure, in addition to the processing illustrated in FIG. 5, 7, 11, or 12. Moreover, the image processing apparatus 10 may further perform at least one of pieces of the processing illustrated in FIGS. 13 and 15.

In the example illustrated in the present figure, the risk information generation unit 120 stores, in the storage unit 150 for each of the plurality of image capturing apparatuses 20, i.e., for each of a plurality of target regions, at least one of a history of past infection risk information and a result of statistically processing the history. Note that, the plurality of target regions are related to each other in a person flow. As one example, the plurality of target regions may adjoin each other, or may be along the same road or railroad (subway).

Then, when the storage unit 150 only stores a history of past infection risk information, the risk information generation unit 120 statistically processes the history. Then, the risk information generation unit 120 generates an estimation result of infection risk information at a predetermined future timing, by use of a result of statistically processing the history of the infection risk information, and current infection risk information. The predetermined timing may be, for example, one hour later, three hours later, or five hours later, but is preferably within 24 hours. The result of statistically processing the history is, for example, a model generated by machine learning, but is not limited thereto. Note that, the model outputs an estimation result of infection risk information at a predetermined future timing, when current infection risk information is input.

First, the risk information generation unit 120 processes a current image generated by each of the plurality of image capturing apparatuses 20 installed in target regions differing from each other, and thereby generates current infection risk information of each of a plurality of the target regions (step S210). In this instance, the risk information generation unit 120 may further process an image generated between a current time and a time before a predetermined time.

Next, the risk information generation unit 120 acquires a result of statistically processing a history of infection risk information, in each of the plurality of target regions. The acquisition may be performed by reading from the storage unit 150, or may be performed by statistically processing a history of infection risk information in situ. Next, the risk information generation unit 120 generates an estimation result of infection risk information at a predetermined future timing, by use of the result of statistically processing the history of the infection risk information, and current infection risk information (step S220).

Next, the display control unit 130 generates display information for displaying current infection risk information and an estimation result of infection risk information at a predetermined future timing, generated by the risk information generation unit 120 (step S230). The display unit 140 displays, by use of the display information, the current infection risk information, and the estimation result of infection risk information at the predetermined future timing (step S240). A person who has seen the display can bring a timing when he/she takes action (e.g., a timing of boarding a train or a timing of going to a destination) to a timing when an infection risk is low.

Note that, when generating an estimation result of infection risk information at a predetermined future timing, the risk information generation unit 120 may determine a tendency of increase and decrease of current infection risk information instead of statistical processing, and use a result of the determination. The risk information generation unit 120 determines the tendency of increase and decrease, for example, by using transition of the number of times that a first distance from past to present is equal to or less than a criterion value.

Figure 17:
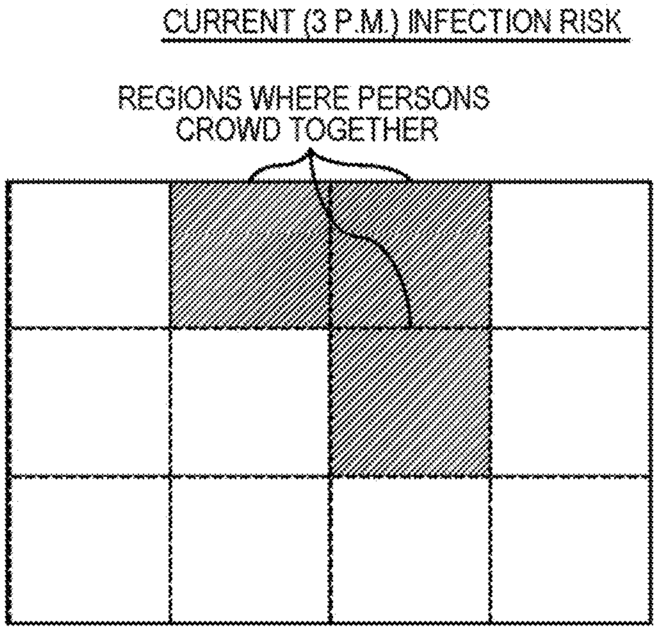
FIG. 17 is a diagram illustrating current infection risk information displayed on the display unit.

FIG. 17 illustrates current infection risk information displayed on the display unit 140. As described above, the risk information generation unit 120 generates infection risk information for each of a plurality of target regions. In the example illustrated in the present figure, a plurality of target regions are regions divided from one large region. Then, the display control unit 130 causes the display unit 140 to display a target region where a risk indicated by the infection risk information is equal to or more than a criterion value, in a state being identifiable from another target region. Note that, the display control unit 130 may cause, in the processing, transition of infection risk information from past to present to be displayed.

Figure 18:
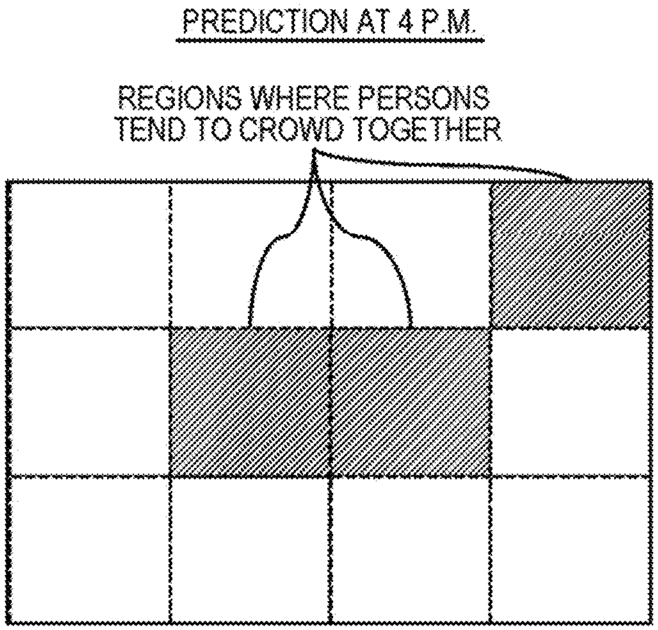
FIG. 18 is a diagram illustrating future infection risk information displayed on the display unit.

FIG. 18 illustrates future infection risk information displayed on the display unit 140. In the example illustrated in the present figure, the display control unit 130 causes the display unit 140 to display a target region where a risk indicated by future infection risk information is equal to or more than a criterion value, in a state being identifiable from another target region. Herein, in a case where a plurality of target regions are related to each other in a person flow, when future infection risk information of a certain target region is generated, current infection risk information around the target region can be used. This is because a person being present in a certain target region may move to another target region several hours later.

Note that, displays illustrated in FIGS. 17 and 18 may be disclosed on the Internet, or may be included in a broadcast content of a television.

As above, according to the present example embodiment, the image processing unit 110 of the image processing apparatus 10 acquires and processes an image generated by the image capturing apparatus 20, i.e., an image including a plurality of persons, and thereby computes, regarding at least some of the plurality of persons, a distance (first distance) to a person being nearest to the person. Then, the control unit 160 causes a predetermined apparatus to execute predetermined control, when a proximity index satisfies a criterion. For example, in a situation where a risk of contracting an infectious disease is high, the control unit 160 can cause the display unit 140 to display information proposing to close an entrance gate and limit entrance into a target region, increase the number of running cash registers of a store, or increase the number of windows in a safety inspection area of an airport, as a measure of reducing a risk of contracting an infectious disease. This can make it easy to recognize or execute a means for reducing a possibility of contracting an infectious disease in a place to be a target.

Moreover, the risk information generation unit 120 generates, by use of a first distance, infection risk information in a target region being a capture target of the image capturing apparatus 20. Thus, a risk of contracting an infectious disease in a target region can be easily recognized.

Moreover, the risk information generation unit 120 outputs a place where a proximity index being an index relating to a proximity state of a plurality of persons satisfies a criterion. The output is displayed on, for example, the display unit 140. This makes it easy to recognize a place where there is a possibility of contracting an infectious disease.

Second Example Embodiment

Figure 19:
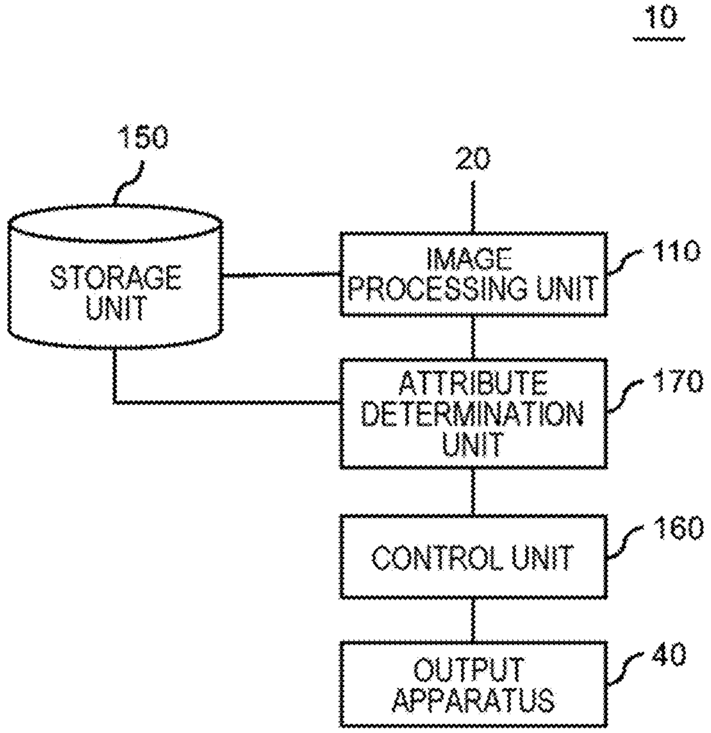
FIG. 19 is a diagram illustrating one example of a functional configuration of the image processing apparatus.

FIG. 19 is a diagram illustrating one example of a functional configuration of an image processing apparatus 10. The image processing apparatus 10 according to the present example embodiment differs from the example embodiment described above in including a configuration that proposes at least one of movement and placement of a person according to an attribute of a person captured in an image. The image processing apparatus 10 illustrated in the present figure includes an image processing unit 110, an attribute determination unit 170, and a control unit 160.

The image processing unit 110 processes an image capturing a person to be moved to or placed in a predetermined place, and thereby determines an attribute of the person captured in the image. The attribute is, for example, age, gender, or the like of each person. Further, the image processing unit 110 may determine, as an attribute, presence or absence of an injury of each person, presence or absence of utilization of a wheelchair or a crutch, or the like.

The attribute determination unit 170 further determines an attribute of each person, based on an attribute determined by the image processing unit 110.

Namely, an attribute of a person determined by the attribute determination unit 170 preferably includes information necessary for a person being associated with an attribute of an evacuation site to be appropriately assigned. For example, an infant is preferably assigned to an evacuation site with an attribute of having equipment for enabling to prepare formula or a suckling room. Thus, the attribute determination unit 170 may further determine that a person determined by the image processing unit 110 to be at an age of less than one is an infant. Further, when the image processing unit 110 determines that a person holding the infant is a woman and in her thirties, the attribute determination unit 170 may determine that the woman is a mother of the infant. Further, the attribute determination unit 170 may determine that a person who is a man beside the mother (a first distance is less than 30 cm) and in his thirties is a father.

In another example, a user of a wheelchair is preferably assigned to an evacuation site being complete with barrier-free equipment. Thus, the attribute determination unit 170 determines, to be a wheelchair user, a person determined by the image processing unit 110 to be on a wheelchair.

The attribute determination unit 170 may further group a plurality of persons, based on an attribute determined by the image processing unit 110, and determine a personnel organization (family organization), based on an attribute of each person within the group. The attribute determination unit 170 may group a plurality of persons by receiving an operational input of bringing the plurality of persons into the same group, or may group, by image processing, a set of persons for whom a first distance is equal to or less than a criterion value. It is assumed that the criterion value in this instance is a value smaller than a criterion value used when infection risk information is generated in the example embodiment described above, for example, equal to or less than 30 cm.

Further, the attribute determination unit 170 may receive an operational input regarding a more detailed attribute of each person. A manager or each person may be caused to input various pieces of attribute information in an evacuation site, a public office, or the like by use of an operation terminal (e.g., a smartphone or a tablet terminal) in such a way as to answer various questions in an input screen (not illustrated).

Further, each person may access a website disclosed on the Internet at or away from home by use of a terminal, and be caused to input various pieces of attribute information in such a way as to answer various questions in an input form. Then, the attribute determination unit 170 can receive the attribute information input in the input form. When each person is at or away from home, the image processing unit 110 may acquire an image to be a processing target, by causing each person to capture a photograph of each person by use of a camera of a terminal of each person, and upload a captured image onto a website.

The attribute determination unit 170 acquires the operationally input attribute information of each person, and determines an attribute of each person. To be specific, attribute information to be acquired may include information such as a past history of each person, a current sick and injury state (including high blood pressure, diabetes, bone fracture, injury, infection status, and antibody information), presence or absence of an allergy, presence or absence of utilization of a diaper, necessity of formula, breast milk, or baby food, and presence or absence of diet restriction.

The control unit 160 causes an output apparatus 40 to output information proposing, according to the attribute determined by the attribute determination unit 170, at least one of movement and placement of the person in such a way that the predetermined place is brought into a predetermined state. One example of the output apparatus 40 is a display unit 140 in FIG. 7.

The predetermined place is, for example, an evacuation place where a person gathers at a disaster or the like. The evacuation place is, for example, a school (a classroom or a gymnasium), a public facility, a hotel, an office, a warehouse, or the like. When a disaster or the like occurs, each of persons evacuates to a nearest evacuation place. A person captured in an image targeted for image processing by the image processing unit 110 includes at least one of (1) a person who has already evacuated to an evacuation place, (2) a person who has evacuated to an evacuation place, and is standing in line at a reception, (3) a person gathering in a predetermined place in order to evacuate to an evacuation place from now, and (4) a person who is about to evacuate to an evacuation place from now. In this example, the control unit 160 performs allocation of an evacuation destination of a person in such a way that an infection risk of each evacuation place does not heighten. In a simplest example, the control unit 160 performs allocation of an evacuation destination in such a way as not to exceed the number of accommodated persons of each evacuation place.

Regarding each evacuation place, attribute information 152 thereof is stored in a storage unit 150. The attribute information 152 of the evacuation place includes, for example, at least one piece of information such as the number of accommodated persons, arrangement of each room (whether to be close to an exit and an entrance, or a rest room), barrier-free appropriateness, presence or absence of a stairway, an elevator, or an escalator, equipment (presence or absence of a suckling room or a rest room for a wheelchair), or presence or absence of residence of a nurse, a doctor, a public health nurse, or the like.

FIG. 20 is a diagram illustrating one example of a data structure of the attribute information 152 of each evacuation site. In this example, for example, identification information of each evacuation site, the number of accommodated persons, information indicating whether equipment being compliant with a wheelchair is provided (e.g., "1" when compliant, and "0" when not compliant), information indicating whether equipment being compliant with an infant is provided (e.g., "1" when compliant, and "0" when not compliant), and the like are stored. The control unit 160 can allocate, based on the attribute information 152, an evacuation destination suited to each person.

Moreover, in another example, an attribute (e.g., an infant, an aged person, a wheelchair user, or the like) of a person may be associated, on an association table, with a necessary attribute of an evacuation site (e.g., a suckling room and residence of a public health nurse for an infant, barrier-free application and residence of a nurse for an aged person, presence or absence of a wheelchair-compliant rest room to a wheelchair user, or the like). The attribute determination unit 170 may determine a necessary attribute of an evacuation site being associated with an attribute of each determined person, and the control unit 160 may extract an evacuation site having the attribute as a candidate from the attribute information 152.

An extracted evacuation place becomes a candidate for an evacuation destination of the person. The control unit 160 may cause the display unit 140 to display information of the extracted evacuation place as an evacuation destination of the person.

Display of the above-described information by the control unit 160 may be performed for each person, for each group (family), for each predetermined number of persons, or for each predetermined period. For example, an attribute may be determined by a unit of one person or a family, and an evacuation destination may be presented to the person or family (e.g., displayed on the display unit 140). Alternatively, attribute information of a plurality of persons is received in a predetermined period, for example, in a morning, and a result of allocating an evacuation destination to each of a plurality of persons received in the period may be presented (e.g., printed and output by a printer (not illustrated)).

Figure 21:
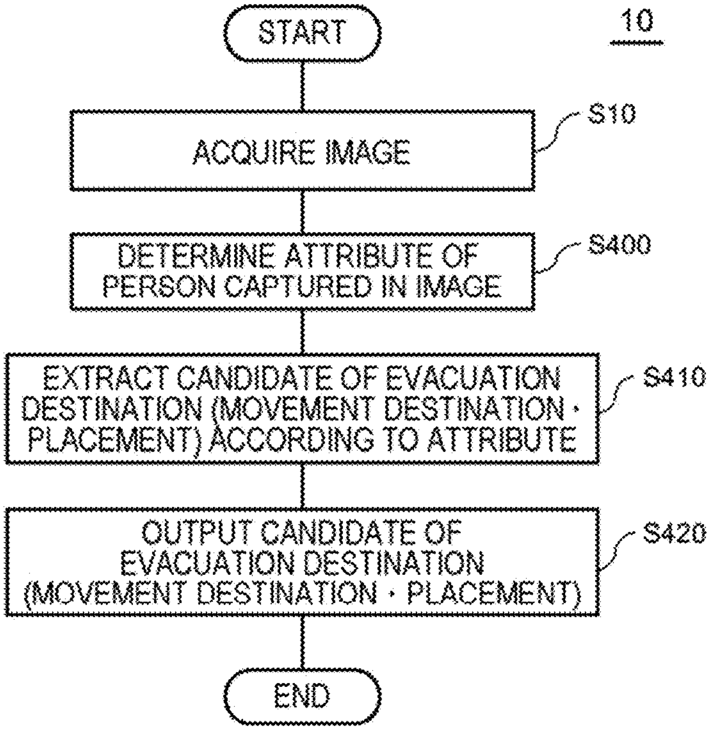
FIG. 21 is a flowchart illustrating an eighth example of processing to be performed by the image processing apparatus.

FIG. 21 is a flowchart illustrating an eighth example of processing to be performed by the image processing apparatus 10. The image processing apparatus 10 also performs processing illustrated in the present figure, in addition to the processing illustrated in FIG. 5, 7, 11, 12, or 16. Moreover, the image processing apparatus 10 may further perform at least one of pieces of the processing illustrated in FIGS. 13 and 15.

In the example illustrated in the present figure, the image processing unit 110 determines an attribute of a person captured in an image (e.g., gender and age, presence or absence of utilization of a wheelchair, or the like), and the attribute determination unit 170 further determines a detailed attribute (an infant and a family (a mother and a father) or the like) of each person (step S400). Then, the attribute determination unit 170 stores the attribute information 152 of each target region (an evacuation site in this example) in the storage unit 150. Note that, the plurality of target regions (evacuation sites) are related to each other in a person flow. As one example, the plurality of target regions may adjoin each other, or may be along the same road or railroad (subway).

Then, the control unit 160 refers to the attribute information 152, and extracts an evacuation site being associated with the determined attribute of the person (step S410). The control unit 160 causes the display unit 140 to display at least one evacuation site as a candidate of an evacuation destination (step S420).

Figure 22:
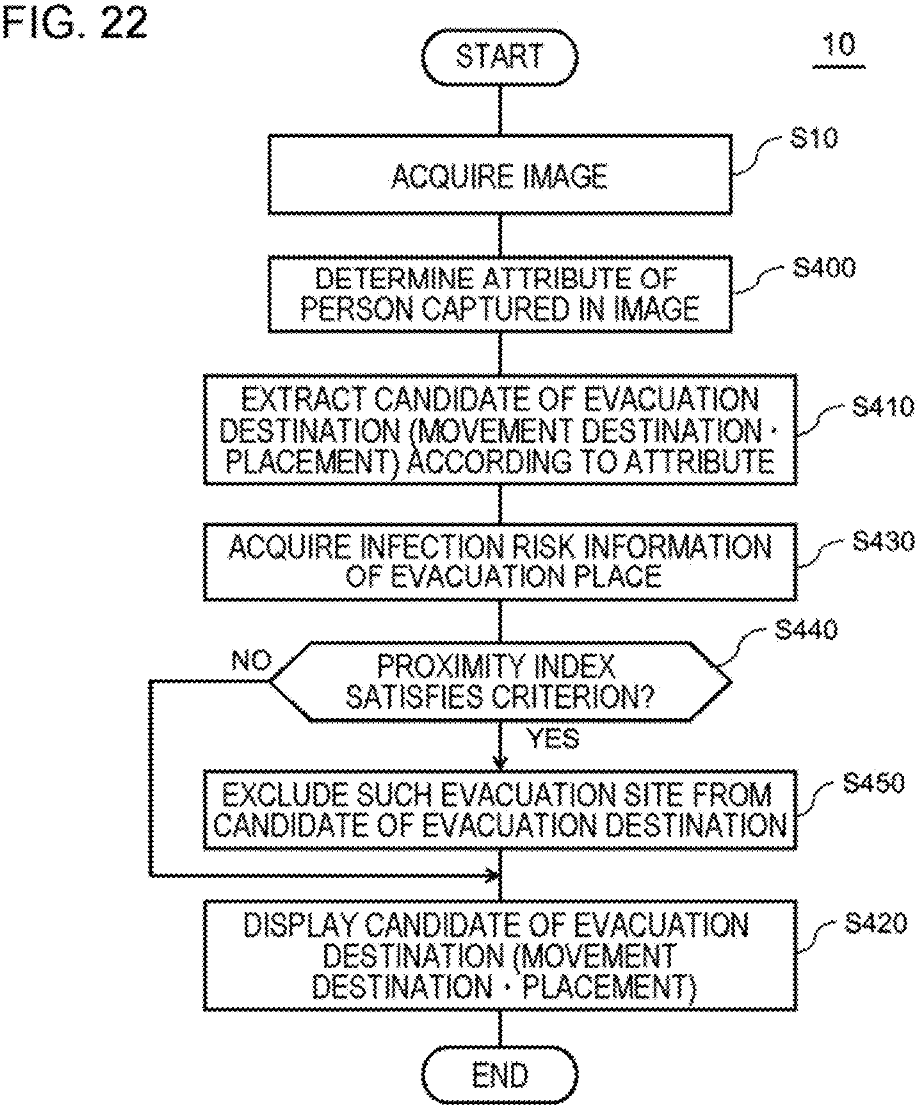
FIG. 22 is a flowchart illustrating a ninth example of processing to be performed by the image processing apparatus.

FIG. 22 is a flowchart illustrating a ninth example of processing to be performed by the image processing apparatus 10. In this example, steps S430 to S450 are provided between steps S410 and S420 of the flowchart in FIG. 21. The image processing apparatus 10 also performs processing illustrated in the present figure, in addition to the processing illustrated in FIG. 5, 7, 11, 12, or 16. Moreover, the image processing apparatus 10 may further perform at least one of pieces of the processing illustrated in FIGS. 13 and 15. In this example, the image processing apparatus 10 further includes a risk information generation unit 120 in FIG. 2.

In relation to extracted evacuation place, the control unit 160 acquires infection risk information generated by the risk information generation unit 120 in the example embodiment described above (step S430). To be specific, first, with each evacuation place as a target region, infection risk information is generated by the risk information generation unit 120. Processing in steps S440 and S450 may be repeatedly executed for each candidate of the evacuation place extracted in step S410. The control unit 160 refers to infection risk information of an evacuation site in the storage unit 150, and, when a proximity index of the evacuation site satisfies a criterion (YES in step S440), excludes the evacuation site from a candidate of an evacuation destination (step S450). Namely, an evacuation site where many persons have already evacuated and an infection risk is heightened is excluded from a candidate of an evacuation destination. Then, the control unit 160 causes the display unit 140 to display a candidate of an evacuation destination (step S420). When a proximity index does not satisfy a criterion (No in step S440), step S450 is bypassed, and an advance is made to step S420.

Moreover, in this example, since a predetermined place is an evacuation site where persons evacuate at a disaster or the like, the control unit 160 preferably performs allocation of an evacuation destination of each person in such a way that a risk of contracting an infectious disease in the evacuation site does not satisfy a criterion, i.e., in such a way that an infection risk does not heighten, or in such a way that a safety ratio of not contracting an infectious disease does not lower. A condition during allocation is, for example, exemplified below, but is not limited thereto.

(Condition example 1) Allocate in such a way as not to exceed the number of accommodated persons of an evacuation site.

(Condition example 2) Allocate to an evacuation site having equipment suitable to an attribute of a person.

(Condition example 3) Allocate to an evacuation site in which a movement distance (computed from an address between evacuation sites) from a current location (position information is acquired from position information of an image capturing apparatus 20, a portable terminal, or the like) to an evacuation site, and a movement means (determined from information of a nearest railway line, station, bus stop, or the like) are suitable to an attribute of a person.

(Condition example 4) Allocate, to the same evacuation site, an aged person or a person who is at higher risk of contracting an infectious disease such as high blood pressure, diabetes, or the like than an able-bodied person. Alternatively, allocate to an evacuation site with a lower infection risk than another evacuation site (the number of accommodated persons being less than a predetermined number of persons, or the like). This heightens a possibility that a person being at high risk of contracting an infectious disease can be protected from a risk of contracting an infectious disease.

Moreover, a criterion of a proximity index of a person (e.g., an aged person, or a person with high blood pressure or diabetes) having an attribute with an infection risk higher than an able-bodied person, and a criterion of a proximity index of an able-bodied person may be varied. For example, a criterion of a person with a high infection risk is set to be lower than a criterion of an able-bodied person. Namely, regarding a person with a high infection risk, an evacuation site with a lower degree of a dense state than a criterion can be determined as a candidate of an evacuation destination, by excluding, from a candidate of an evacuation destination, an evacuation site at a phase where a degree of a dense state of the evacuation site is lower than an able-bodied person.

Moreover, the control unit 160 may cause the display unit 140 to display current infection risk information of an evacuation site determined as a candidate. A person in charge may confirm a current situation, and then instruct an evacuation destination. Further, the control unit 160 may cause the display unit 140 to display the attribute information 152 of an evacuation site determined as a candidate.

As above, according to the present example embodiment, the image processing unit 110 of the image processing apparatus 10 processes an image capturing a person to be moved to or placed in a predetermined place, and thereby determines an attribute of the person captured in the image. Then, the attribute determination unit 170 further determines an attribute of each person, based on an attribute determined by the image processing unit 110. The attribute determination unit 170 determines, for example, an attribute of a person such as an infant or a wheelchair user for whom an evacuation site having specific equipment is desirably determined as an evacuation destination. Thus, the control unit 160 extracts, as a candidate of an evacuation destination, an evacuation site having an attribute suited to an attribute of the person, and causes the display unit 140 to display the extracted candidate. Thus, a person who has evacuated can be allocated to an appropriate evacuation site. Then, the control unit 160 collects, to the same evacuation destination, a person such as an aged person being particularly at high risk of contracting an infectious disease, or selects, as an evacuation destination, an evacuation site with a small number of accommodated persons, i.e., a place where a risk of contracting an infectious disease is low, and outputs the evacuation destination. Thus, a person being at high risk of contracting an infectious disease can be protected, and a possibility that spread of infection can be prevented heightens. This can make it easy to recognize or execute a means for reducing a possibility of contracting an infectious disease in a place to be a target.

While the example embodiments of the present invention have been described above with reference to the drawings, the example embodiments are exemplifications of the present invention, and various configurations other than those described above can also be adopted.

Moreover, although a plurality of processes (pieces of processing) are described in order in a plurality of flowcharts used in the above description, an execution order of processes executed in each example embodiment is not limited to the described order. In each example embodiment, an order of illustrated processes can be changed to an extent that causes no problem in terms of content. Moreover, each example embodiment described above can be combined to an extent that content does not contradict.

Moreover, when information relating to a person is acquired and utilized in the present invention, the acquisition and utilization are legally performed.

Some or all of the above-described example embodiments can also be described as, but are not limited to, the following supplementary notes.

1. An image processing apparatus including:
   an image processing unit that processes an image of a target region, and thereby computes a proximity index being an index relating to a proximity state of a plurality of persons captured in the image; and
   a control unit that causes a predetermined apparatus to execute predetermined control, when the proximity index satisfies a criterion.
2. The image processing apparatus according to supplementary note 1, wherein
   the control unit causes an output apparatus to output information relating to the proximity index of the target region.
3. The image processing apparatus according to supplementary note 1 or 2, wherein
   the image processing unit
      computes, for each of the persons, a first distance being a distance to the person being nearest to the person, and
      counts a number of times that the first distance is equal to or less than a criterion value, and
   the proximity index is set by use of the number of times that the first distance is equal to or less than the criterion value.
4. The image processing apparatus according to supplementary note 3, wherein
   the proximity index is a criterion value set for the number of times,
   a plurality of values are set as the criterion values, and
   the control unit causes an output apparatus to output information indicating the value satisfied by the number of times in the target region, together with the information relating to the proximity index of the target region.
5. The image processing apparatus according to supplementary note 3 or 4, wherein
   the image processing unit processes the images generated at a plurality of timings, and thereby computes, when detecting a state where the first distance is equal to or less than a criterion value, a time in which the state continues, and
   the proximity index is set by use of a number of times that the state where the first distance is equal to or less than the criterion value continues for equal to or more than a criterion time.
6. The image processing apparatus according to any one of supplementary notes 1 to 5, wherein
   the predetermined apparatus is an entrance gate to the target region, and
   the control unit closes the entrance gate when the proximity index satisfies a criterion.
7. The image processing apparatus according to any one of supplementary notes 1 to 6, wherein,
   when the proximity index satisfies the criterion, the control unit causes an output apparatus to output measure information indicating a measure for bringing the target region into a predetermined state.
8. The image processing apparatus according to any one of supplementary notes 1 to 7, wherein
   the image processing unit further determines an attribute of the person captured in the image, and
   the control unit causes an output apparatus to output information proposing, according to the determined attribute, at least one of movement and placement of the person in such a way that the target region is brought into a predetermined state.
9. The image processing apparatus according to supplementary note 8, wherein
   the target region includes a plurality of places, and
   the control unit further causes an output apparatus to output information proposing, according to the attribute of each place of the target region, at least one of movement and placement of the person in each of the places in such a way that each of the places of the target region is brought into a predetermined state.

10. The image processing apparatus according to any one of supplementary notes 1 to 9, wherein
the image is an image capturing a facility.

11. The image processing apparatus according to supplementary note 10, wherein
the facility is a shopping mall, an airport, a station, a hospital, or a store.

12. An image processing method including,
performing, by a computer:
image processing of processing an image of a target region, and thereby computing a proximity index being an index relating to a proximity state of a plurality of persons captured in the image; and
control processing of causing a predetermined apparatus to execute predetermined control, when the proximity index satisfies a criterion.

13. The image processing method according to supplementary note 12, further including,
by the computer,
in the control processing, causing an output apparatus to output information relating to the proximity index of the target region.

14. The image processing method according to supplementary note 12 or 13, further including,
by the computer:
in the image processing,
computing, for each of the persons, a first distance being a distance to the person being nearest to the person; and
counting a number of times that the first distance is equal to or less than a criterion value, wherein
the proximity index is set by use of the number of times that the first distance is equal to or less than the criterion value.

15. The image processing method according to supplementary note 14, wherein
the proximity index is a criterion value set for the number of times, and
a plurality of values are set as the criterion values,
the image processing method further including,
by the computer,
in the control processing, causing an output apparatus to output information indicating the value satisfied by the number of times in the target region, together with the information relating to the proximity index of the target region.

16. The image processing method according to supplementary note 14 or 15, further including,
by the computer,
in the image processing, processing the image generated at a plurality of timings, and thereby computing, when detecting a state where the first distance is equal to or less than a criterion value, a time in which the state continues, wherein
the proximity index is set by use of a number of times that the state where the first distance is equal to or less than the criterion value continues for equal to or more than a criterion time.

17. The image processing method according to any one of supplementary notes 12 to 16, wherein
the predetermined apparatus is an entrance gate to the target region,
the image processing method further including,
by the computer,
in the control processing, closing the entrance gate when the proximity index satisfies a criterion.

18. The image processing method according to any one of supplementary notes 12 to 17, further including,
by the computer,
in the control processing, when the proximity index satisfies the criterion, causing an output apparatus to output measure information indicating a measure for bringing the target region into a predetermined state.

19. The image processing method according to any one of supplementary notes 12 to 18, further including,
by the computer:
in the image processing, further determining an attribute of the person captured in the image; and
in the control processing, causing an output apparatus to output information proposing, according to the determined attribute, at least one of movement and placement of the person in such a way that the target region is brought into a predetermined state.

20. The image processing method according to supplementary note 19, wherein
the target region includes a plurality of places,
the image processing method further including,
by the computer,
in the control processing, further causing an output apparatus to output information proposing, according to the attribute of each place of the target region, at least one of movement and placement of the person in each of the places in such a way that each of the places of the target region is brought into a predetermined state.

21. The image processing method according to any one of supplementary notes 12 to 20, wherein
the image is an image capturing a facility.

22. The image processing method according to supplementary note 21, wherein
the facility is a shopping mall, an airport, a station, a hospital, or a store.

23. A program causing a computer to include:
an image processing function of processing an image of a target region, and thereby computing a proximity index being an index relating to a proximity state of a plurality of persons captured in the image; and
a control function of causing a predetermined apparatus to execute predetermined control, when the proximity index satisfies a criterion.

24. The program according to supplementary note 23, wherein
the control function causes an output apparatus to output information relating to the proximity index of the target region.

25. The program according to supplementary note 23 or 24, wherein
the image processing function
computes, for each of the persons, a first distance being a distance to the person being nearest to the person, and
counts a number of times that the first distance is equal to or less than a criterion value, and
the proximity index is set by use of the number of times that the first distance is equal to or less than the criterion value.

26. The program according to supplementary note 25, wherein
the proximity index is a criterion value set for the number of times,
a plurality of values are set as the criterion values, and the control function causes an output apparatus to output information indicating the value satisfied by the number of times in the target region, together with the information relating to the proximity index of the target region.

27. The program according to supplementary note 25 or 26, wherein the image processing function processes the images generated at a plurality of timings, and thereby computes, when detecting a state where the first distance is equal to or less than a criterion value, a time in which the state continues, and the proximity index is set by use of a number of times that the state where the first distance is equal to or less than the criterion value continues for equal to or more than a criterion time.

28. The program according to any one of supplementary notes 23 to 27, wherein the predetermined apparatus is an entrance gate to the target region, and the control function closes the entrance gate when the proximity index satisfies a criterion.

29. The program according to any one of supplementary notes 23 to 28, wherein when the proximity index satisfies the criterion, the control function causes an output apparatus to output measure information indicating a measure for bringing the target region into a predetermined state.

30. The program according to any one of supplementary notes 23 to 29, wherein the image processing function further determines an attribute of the person captured in the image, and, in the control function, causing an output apparatus to output information proposing, according to the determined attribute, at least one of movement and placement of the person in such a way that the target region is brought into a predetermined state.

31. The program according to supplementary note 30, wherein the target region includes a plurality of places, and the control function further causes an output apparatus to output information proposing, according to the attribute of each place of the target region, at least one of movement and placement of the person in each of the places in such a way that each of the places of the target region is brought into a predetermined state.

32. The program according to any one of supplementary notes 23 to 31, wherein the image is an image capturing a facility.

33. The program according to supplementary note 32, wherein the facility is a shopping mall, an airport, a station, a hospital, or a store.

34. An image processing apparatus including:

an image processing unit that processes an image capturing a person to be moved to or placed in a predetermined place, and thereby determines an attribute of the person captured in the image; and a control unit that causes an output apparatus to output information proposing, according to the determined attribute, at least one of movement and placement of the person in such a way that the predetermined place is brought into a predetermined state.

35. The image processing apparatus according to supplementary note 34, wherein the predetermined place includes a plurality of places, and the control unit further causes the output apparatus to output information proposing, according to the attribute of each of the places, at least one of movement and placement of the person in each of the places in such a way that each of the places is brought into a predetermined state.

36. The image processing apparatus according to supplementary note 34 or 35, wherein the image processing unit processes an image of each of the places, and thereby computes a proximity index being an index relating to a proximity state of a plurality of persons captured in the image, and the control unit excludes the place from a target of movement and placement of the person in the proposing information, when the proximity index satisfies a criterion.

37. An image processing method including, performing, by a computer:

image processing of processing an image capturing a person to be moved to or placed in a predetermined place, and thereby determining an attribute of the person captured in the image; and output control processing of causing an output apparatus to output information proposing, according to the determined attribute, at least one of movement and placement of the person in such a way that the predetermined place is brought into a predetermined state.

38. The image processing method according to supplementary note 37, wherein the predetermined place includes a plurality of places, the image processing method further including, by the computer, in the output control processing, further causing the output apparatus to output information proposing, according to the attribute of each of the places, at least one of movement and placement of the person in each of the places in such a way that each of the places is brought into a predetermined state.

39. The image processing method according to supplementary note 37 or 38, further including, by the computer:

in the image processing, processing an image of each of the places, and thereby computing a proximity index being an index relating to a proximity state of a plurality of persons captured in the image; and, in the output control processing, excluding the place from a target of movement and placement of the person in the proposing information, when the proximity index satisfies a criterion.

40. A program causing a computer to include:

an image processing function of processing an image capturing a person to be moved to or placed in a predetermined place, and thereby determining an attribute of the person captured in the image; and a control function of causing an output apparatus to output information proposing, according to the determined attribute, at least one of movement and placement of the person in such a way that the predetermined place is brought into a predetermined state.

41. The program according to supplementary note 40, wherein the predetermined place includes a plurality of places, and the control function further causes the output apparatus to output information proposing, according to the attribute of each of the places, at least one of movement and placement of the person in each of the places in such a way that each of the places is brought into a predetermined state.

42. The program according to supplementary note 40 or 41, wherein the image processing function processes an image of each of the places, and thereby computes a proximity index being an index relating to a proximity state of a plurality of persons captured in the image, and the control function excludes the place from a target of movement and placement of the person in the proposing information, when the proximity index satisfies a criterion.

This application is based upon and claims the benefit of priority from Japanese patent application No. 2020-098402, filed on Jun. 5, 2020, the disclosure of which is incorporated herein in its entirety by reference.

REFERENCE SIGNS LIST

10 Image processing apparatus
20 Image capturing apparatus
110 Image processing unit
120 Risk information generation unit
130 Display control unit
140 Display unit
150 Storage unit
160 Control unit
170 Attribute determination unit

The invention claimed is:

1. An image processing apparatus comprising:

at least one memory storing instructions; and at least one processor configured to execute the instructions to:

acquire an image capturing a target region generated by an image capturing apparatus;

acquire attribute information indicating at least a number of persons corresponding to the target region;

process the acquired image to obtain a number of persons in the target region and to determine an attribute of each person captured in the image;

determine whether the obtained number of persons exceeds the number of persons of the attribute information;

in a case where the number of persons in the target region exceeds the number of persons of the attribute information, display, on a display apparatus, at least one piece of information guiding from the target region to another place, and information urging to exit from the target region; and cause the display apparatus to display information proposing, according to the determined attribute, at least one of movement and placement of the each person in such a way that a predetermined place is brought into a predetermined state.

2. The image processing apparatus according to claim 1, wherein the target region is multiple, and the at least one processor is configured to execute the instructions to perform allocation of persons in such a way as not to exceed the number of persons in each of the target regions.

3. The image processing apparatus according to claim 1, wherein the at least one processor is configured to execute the instructions to sequentially process images in real time as the images are acquired.

4. The image processing apparatus according to claim 1, wherein the at least one processor is configured to execute the instructions to:

store the acquired images in a storage; and process the images read from the storage.

5. The image processing apparatus according to claim 1, wherein one of the target region is divided into a plurality of parts.

6. The image processing apparatus according to claim 1, wherein the at least one processor is configured to execute the instructions to:

in a case where the number of persons in the target region exceeds the number of persons of the attribute information, close an entrance gate of the target region.

7. An image processing method performed by a computer and comprising:

acquiring an image capturing a target region generated by an image capturing apparatus;

acquiring attribute information indicating at least a number of persons corresponding to the target region;

processing the acquired image to obtain a number of persons in the target region and to determine an attribute of each person captured in the image;

determining whether the obtained number of persons exceeds the number of persons of the attribute information;

in a case where the number of persons in the target region exceeds the number of persons of the attribute information, displaying, on a display apparatus, at least one piece of information guiding from the target region to another place, and information urging to exit from the target region; and causing the display apparatus to display information proposing, according to the determined attribute, at least one of movement and placement of the each person in such a way that a predetermined place is brought into a predetermined state.

8. A non-transitory computer-readable storage medium storing a program executable by a computer to perform processing comprising:

acquiring an image capturing a target region generated by an image capturing apparatus;

acquiring attribute information indicating at least a number of persons corresponding to the target region;

processing the acquired image to obtain a number of persons in the target region and to determine an attribute of each person captured in the image;

determining whether the obtained number of persons exceeds the number of persons of the attribute information;

in a case where the number of persons in the target region exceeds the number of persons of the attribute information, displaying, on a display apparatus, at least one piece of information guiding from the target region to another place, and information urging to exit from the target region; and causing the display apparatus to display information proposing, according to the determined attribute, at least one of movement and placement of the each person in such a way that a predetermined place is brought into a predetermined state.

* * * * *